US009517041B2

(12) United States Patent
Melman et al.

(10) Patent No.: US 9,517,041 B2
(45) Date of Patent: *Dec. 13, 2016

(54) X-RAY TUBE

(71) Applicant: CONTROLRAD SYSTEMS INC., Radnor, PA (US)

(72) Inventors: Haim Zvi Melman, Kfar Saba (IL); Allon Guez, Pen Valley, PA (US)

(73) Assignee: ControlRad Systems Inc., Radnor, PA (US)

( * ) Notice: Subject to any disclaimer, the term of this patent is extended or adjusted under 35 U.S.C. 154(b) by 195 days.

This patent is subject to a terminal disclaimer.

(21) Appl. No.: 14/489,538

(22) Filed: Sep. 18, 2014

(65) Prior Publication Data

US 2015/0078523 A1   Mar. 19, 2015

Related U.S. Application Data

(63) Continuation-in-part of application No. 13/311,491, filed on Dec. 5, 2011, now abandoned.

(60) Provisional application No. 61/887,471, filed on Oct. 7, 2013.

(51) Int. Cl.
| | |
|---|---|
| A61B 6/06 | (2006.01) |
| A61B 6/00 | (2006.01) |
| A61B 6/10 | (2006.01) |
| G21K 1/02 | (2006.01) |
| A61B 17/00 | (2006.01) |

(52) U.S. Cl.
CPC ............. *A61B 6/469* (2013.01); *A61B 6/06* (2013.01); *A61B 6/107* (2013.01); *A61B 6/4007* (2013.01); *A61B 6/4028* (2013.01); *A61B 6/467* (2013.01); *A61B 6/542* (2013.01); *G21K 1/02* (2013.01); *A61B 2017/00216* (2013.01)

(58) Field of Classification Search
CPC ............. A61B 6/00; A61B 6/06; H04N 5/321; H01J 35/00; H01J 35/02; H01J 35/06; H01J 35/065; H01J 35/08; H01J 35/14; H01J 35/30; H01J 2235/00; H01J 2235/068; H01J 2235/08; H05G 1/52; G21K 1/02; G21K 1/08; G21K 1/087; G21K 1/093; A61N 5/1048; A61N 5/1049; A61N 5/1064; A61N 5/1065; A61N 5/1067
USPC .......... 378/42, 98, 98.2, 113, 124, 134, 137, 378/147, 150, 205
See application file for complete search history.

(56) References Cited

U.S. PATENT DOCUMENTS

| | | | |
|---|---|---|---|
| 6,928,142 B2 * | 8/2005 | Shao .................. | A61B 6/037 250/363.04 |
| 2015/0016589 A1 * | 1/2015 | Melman ............... | H01J 35/14 378/62 |

* cited by examiner

*Primary Examiner* — Jurie Yun
(74) *Attorney, Agent, or Firm* — Manelli Selter PLLC; Edward J. Stemberger

(57) ABSTRACT

An x-ray system comprising: at least one x-ray tube assembly; a collimator; an image detector; a monitor; means for determining the location of a Region of Interest (ROI) of a patient on said displayed image; a first controller; an image processing unit configured to modify the detected image for display on said monitor according to the image parts in said ROI; each x-ray tube assembly comprising a plurality of cathodes; and at least one anode; a second controller configured to control operating parameters of each one of said at least one x-ray tube assembly, said parameters comprising at least one collision location of electrons emitted from said plurality of cathodes on said at least one anode in reference to said collimator aperture; and means for controlling the directions of emitted x-ray beams.

17 Claims, 32 Drawing Sheets

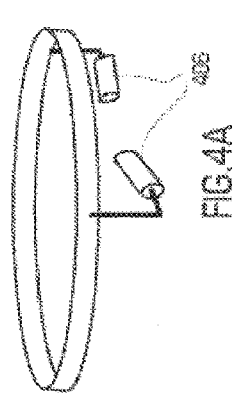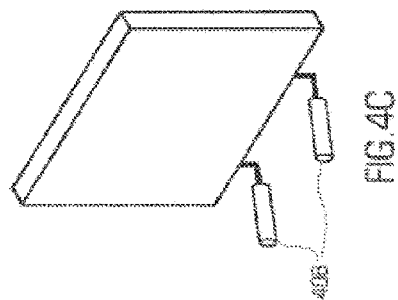

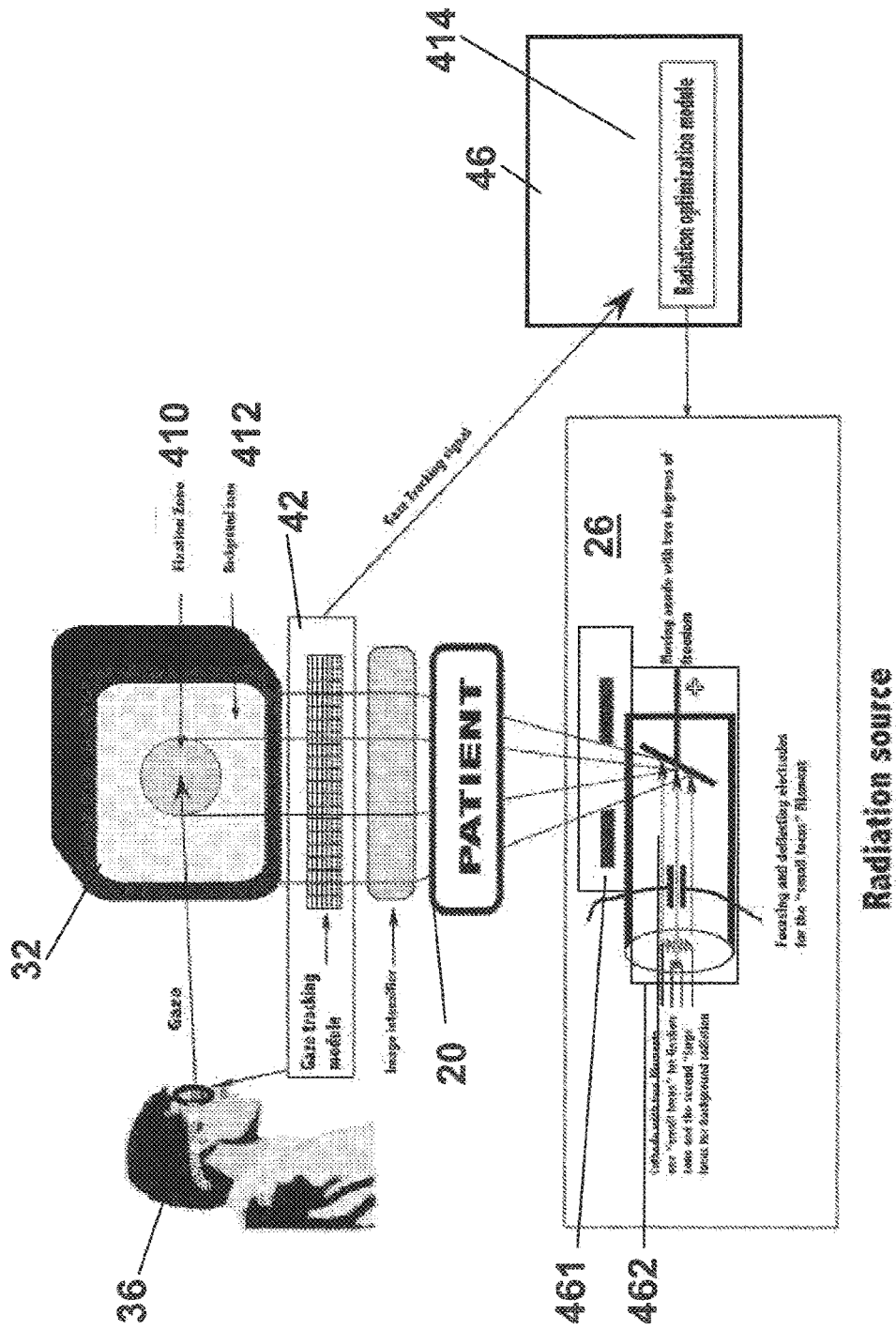

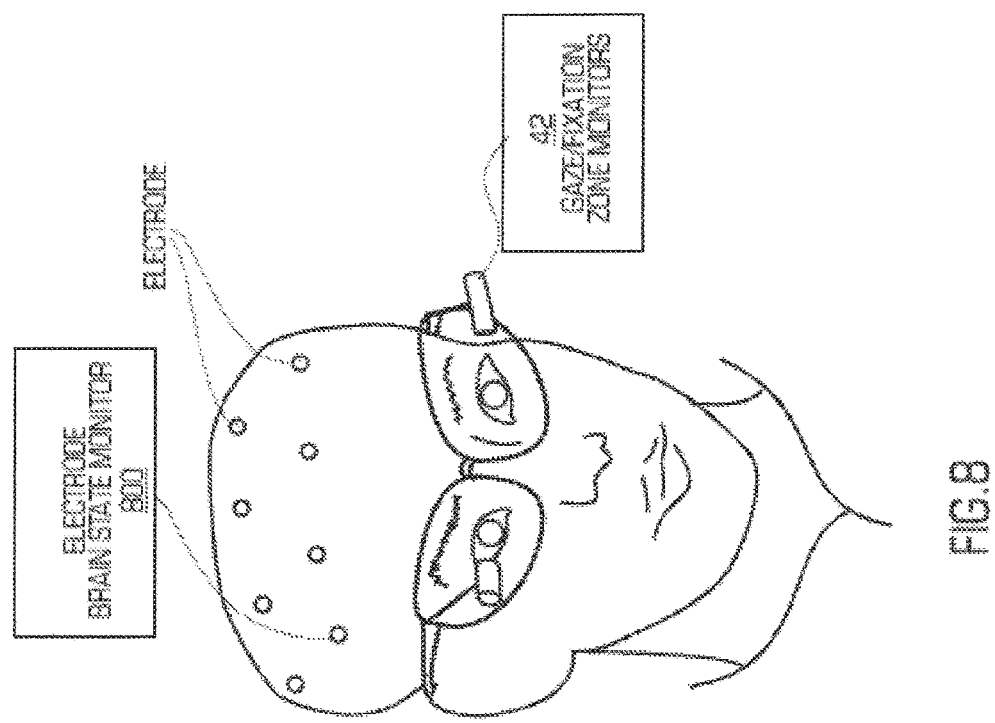

X-RAY TUBE

PRIORITY CLAIMS/RELATED APPLICATIONS

This application is filed as a Continuation-in-Part of U.S. patent application Ser. No. 13/311,491 filed on Dec. 5, 2011, the entirety of which is incorporated herein by reference. This application also claims the benefit under 35 USC 119(e) to U.S. Provisional Patent Application Ser. No. 61/887,471 filed on Oct. 7, 2013 and entitled "X-RAY TUBE", the entirety of which is incorporated herein by reference.

TECHNOLOGY FIELD

The disclosure relates generally to radiation systems (whether for industrial, security, therapeutic use or imaging) and in particular to systems to minimize the radiation to which a patient, a person, an object or an operator is exposed. The disclosure is also related to the field of x-ray tubes and more particularly to the field of creating and controlling x-ray radiation geometry.

BACKGROUND

Devices and system that generate various forms of radiation/ionizing energy are used for various therapeutic/treatment, diagnostic or imaging purposes. For example, various forms of radiation/ionizing energy may be used to inspect an object (such as in airports scanning systems, different security setups, manufacturing and process control) or inspect a patient (such as in a clinic or a hospital, e.g. Cath lab, where a surgeon/therapist operates an X Ray or CT system.)

The medical imaging industry for example is heavily focused on reducing the radiation dose in diagnostic and treatment procedure that include hardware and software modification and operator room procedures. See Miller D L, Balter S, Schueler B A, Wagner L K, Strauss K J, Vano E. "Clinical radiation management for fluoroscopically guided interventional procedures", Radiology. November 2010; 257 (2):321-332. The reporting of radiation dose is one of the QA measurements that are required by Medicare. Furthermore, the Food and Drug Administration in their 2010 "White paper" called for significant reduction of the "unnecessary radiation". FDA, "White Paper: Initiative to Reduce Unnecessary Radiation Exposure from Medical Imaging. In: Administration CfDaRHUSFaD, ed. 2010.

There are two main components that can reduce radiation exposure. The first component is the technical improvements of the x-ray equipment, such as investment in better filtering, collimators, acquisition equipment and image analysis. The other component is the way the operator uses the radiation, which includes the length of exposure, distance from the source to the patient and proper collimation. See Miller D L, Balter S, Schueler B A, Wagner L K, Strauss K J, Vano E. "Clinical radiation management for fluoroscopically guided interventional procedures", Radiology. November 2010; 257(2):321-332 and Arthur W R, Dhawan J, Norell M S, Hunter A J, Clark A L, "Does cardiologist- or radiographer-operated fluoroscopy and image acquisition influence optimization of patient radiation exposure during routine coronary angiography?", Br J Radiol. September 2002; 75(897):748-753. The radiation education of the operator/physician is critical to reduce the radiation dose and trained physician utilize significantly lower amounts of radiation. A similar focus to reduce radiation exposure exists in the non-medical areas. For example, the nuclear industry has been very sensitive for several decades to radiation exposure and in many other manufacturing fields there are strict guidelines for minimizing exposure. See Http://www-.state.il.us/iema/publications/pdf/IEMA%020032%20Everyday%20Uses-%20of%20Radiation.pdf.

For example, during a fluoroscopy guided, interventional medical procedure, there are periods of time when the operator (usually a physician), even when he/she activates the radiation source which radiates the patient and the staff does not receive the information that is generated by a radiation source. This radiation (and the information in it) are not only wasted but are furthermore needlessly damaging to the patient and the staff/operator of the radiation source. This may be referred to as "Unattended Radiation" (UR) which is undesirable. Thus, in the various different applications in which objects or patients are being inspected, it is desirable to reduce the Unattended Radiation and therefore minimize the exposure to the potentially harmful radiation by the operator and/or patient and it is to this end that the disclosure is directed.

Typical x-ray tubes generate x-ray radiation over a relatively wide solid angle. To avoid unnecessary exposure to both the patient and the medical team, collimators of x-ray absorbing materials such as lead are used to block the redundant radiation. This way only the necessary solid angle of useful radiation exits the x-ray tube to expose only the necessary elements.

Such collimators may assume a variety of designs and x-ray radiation geometry. Collimators can be set up manually or automatically using as input, for example, the dimensions of the cassette holding the plate to limit the radiation to the dimensions of the film in the cassette.

In fluoroscopy the situation is more dynamic than in a single exposure x-ray. The x-ray radiation is active for long periods and the treating physician typically has to stand near the patient, therefore near the x-ray radiation. As a result, it is desired to provide methods to minimize exposure to the medical team. Methods for reducing x-ray radiation intensity have been suggested where the resultant reduced signal to noise ratio (S/N) of the x-ray image is compensated by real-time digital image enhancement. Other methods suggest a collimator limiting the solid angle of the x-ray radiation to a fraction of the image intensifier area and moving the collimator to sweep the entire input area of the image intensifier where the Region of Interest (ROI) is exposed more than the rest of the area. This way, the ROI gets high enough x-ray radiation to generate a good S/N image while the rest of the image is exposed with low x-ray intensity, providing a relatively low S/N image. The ROI size and position can be determined in a plurality of methods. For example, it can be a fixed area in the center of the image or it can be centered automatically about the most active area in the image, this activity is determined by temporal image analysis of a sequence of cine images received from the video camera of the fluoroscopic system. Reference is made now to FIG. 9A which presents a typical layout of a fluoroscopy clinical environment.

X-ray tube 100 generates x-ray radiation 102 directed upward occupying a relatively large solid angle towards collimator 104. Collimator 104 blocks a part of the radiation allowing a smaller solid angle of radiation to continue in the upward direction, go through bed 108 that is typically made of material that is relatively transparent to x-ray radiation and through patient 110 who is lying on bed 108. Part of the radiation is absorbed and scattered by the patient and the remaining radiation arrives at the typically round input area 112 of image intensifier 114. The input area of the image intensifier is typically in the order of 300 mm in diameter but may vary per the model and the technology. The image generated by image intensifier 114 is captured by video camera 116 and then displayed on monitor 118 as image 120.

In modern systems the image intensifier and video camera are often replaced by a rectangle flat panel detector. It would be appreciated that the description below referring to image intensifiers and video cameras is analog for the case of a flat panel detector or other detectors converting x-ray radiation to an electronic image.

Operator 122 is standing by the patient to perform the medical procedure while watching image 120.

The operator has a foot-switch 124. When pressing the switch, continuous x-ray radiation is emitted to provide cine imaging 120. The intensity of x-ray radiation is typically optimized in a tradeoff of low x-ray intensity that is desired to reduce exposure to the patient and the operator and high x-ray intensity that is desired to enable a high quality image 120 (high S/N). With low intensity x-ray radiation and thus low exposure of the image intensifier input area, the S/N of image 120 might be so low that image 120 becomes useless.

SUMMARY

According to a first aspect of the present invention there is provided an x-ray system comprising: at least one x-ray tube assembly; a collimator forming an aperture; an image detector; a monitor configured to display detected images; means for determining the location of at least one Region of Interest (ROI) of a patient on said displayed image; a first controller connected with said means for determining the location of said at least one ROI; an image processing unit connected with said image detector, said monitor and said first controller, said image processing unit configured to modify the detected image for display on said monitor according to the image parts in said at least one ROI; each x-ray tube assembly comprising a plurality of cathodes; and at least one anode; a second controller connected with said first controller and with said at least one x-ray tube assembly, said second controller configured to control operating parameters of each one of said at least one x-ray tube assembly, said parameters comprising at least one collision location of electrons emitted from said plurality of cathodes on said at least one anode in reference to said collimator aperture; and means for controlling the directions of emitted x-ray beams.

The means for controlling the directions of emitted x-ray beams may be selected from the group consisting of at least one electromagnetic device and at least one mechanical actuator.

The means for determining the location of said at least one ROI may comprise at least one eye tracker.

The first controller may further be configured to calculate collision locations of electrons emitted from the plurality of cathodes on the at least one anode according to said determined locations of said at least one ROI.

The at least one mechanical actuator may be selected from the group consisting of: electric motors, pneumatic actuators and piezoelectric actuators.

The second controller may be configured to control the means for determining collision location by selectively deploying at least one of: said at least one electromagnetic device, said at least one mechanical actuator and each one of said plurality of cathodes' current.

The each one of said plurality of cathodes' current may be equal to a total current divided by the number of said plurality of cathodes and wherein said electron beams may be directed to the same collision location.

The selectively deploying may comprise deploying at least one of said at least one electromagnetic device and said at least one mechanical actuator according to the movement angles required by said at least one ROI.

The collimator may be configured to form an aperture limiting a solid angle of an x-ray beam emitted from each of said at least one anode.

The current in each of the electromagnetic devices may be set to control a direction of said solid angle of each of said x-ray beams.

The aperture may be movable in a plane generally parallel to a surface of the collimator.

The first controller may further be configured to calculate a location and size of said collimator aperture according to said determined locations of the at least one ROI.

The collimator may be movable in a plane generally perpendicular to a surface of the collimator.

The plurality of cathodes and at least one anode may be encapsulated in a single x-ray tube assembly.

The at least one anode may comprise a plurality of anodes.

The at least one x-ray tube assembly may comprise a plurality of x-ray tube assemblies.

The plurality of cathodes and said plurality of anodes may be encapsulated in said plurality of x-ray tube assemblies wherein each x-ray tube assembly may comprise at least one anode and at least one cathode.

According to a second aspect of the present invention there is provided a method of controlling the directions of x-ray beams emitted from at least one x-ray tube assembly via a collimator forming an aperture by manipulation of the electronic beams of each one of said at least one x-ray tube assembly to control at least one collision location of electrons emitted from a plurality of cathodes on at least one anode, said at least one collision location calculated according to at least one determined ROI, comprising: determining at least one collision location of electrons emitted from said plurality of cathodes on said at least one anode in reference to said collimator aperture; and controlling the directions of emitted x-ray beams.

The controlling the directions of emitted x-ray beams may comprise providing means selected from the group consisting of at least one electromagnetic device near the path of electrons flowing from at least one of said plurality of cathodes to said at least one anode and at least one mechanical actuator.

The method may further comprise selecting a current level to generate a desired magnetic field in said path of the electrons flowing from said at least one cathode to said at least one anode.

The determining the location of said at least one ROI may comprise using at least one eye tracker.

The calculating at least one collision location of electrons emitted from at least one cathode of said plurality of cathodes on the at least one anode may be done according to said determined location of said at least one ROI.

The at least one mechanical actuator may be selected from the group consisting of: electric motors, pneumatic actuators and piezoelectric actuators.

The method may further comprise selectively deploying at least one of said at least one electromagnetic device and said at least one mechanical actuator. The selectively deploying may comprise deploying according to the movement angle required by said at least one ROI.

The method may further comprise using the collimator to form an aperture limiting a solid angle of an x-ray beam emitted from the at least one x-ray tube assembly. The aperture may be movable in a plane generally parallel to a surface of the collimator.

The first controller may be further configured to calculate a location and size of said collimator aperture according to said determined location of said at least one ROI.

The collimator may be movable in a plane generally perpendicular to a surface of the collimator.

The plurality of cathodes and at least one anode may be encapsulated in a single x-ray tube assembly.

The at least one anode may comprise a plurality of anodes.

The at least one x-ray tube assembly may comprise a plurality of x-ray tube assemblies.

The plurality of cathodes and said plurality of anodes may be encapsulated in said plurality of x-ray tube assemblies, wherein each x-ray tube assembly may comprise at least one anode and at least one cathode.

The method may further comprise connecting each one of said plurality of cathodes to a current source; and for each one of said plurality of cathodes, selecting a heating current level to generate an electron beam in a desired electron beam current; wherein said plurality of desired electron beams currents sum up to a total desired electron beam current at the anode; and wherein said plurality of electron beams are directed to the same collision location.

According to a third aspect of the present invention there is provided an x-ray system comprising: at least one x-ray tube assembly; a collimator forming an aperture; an image detector; a monitor configured to display a processed stereoscopic image; means for determining the location of at least one Region of Interest (ROI) of a patient on said displayed image; a first controller connected with said means for determining the location of said at least one ROI; an image processing unit connected with said image detector, said monitor and said first controller, said image processing unit configured to create a stereoscopic image from said detected images and to modify said stereoscopic image for display on said monitor according to the image parts in said at least one ROI; each x-ray tube assembly comprising at least one cathode; and at least one anode; a second controller connected with said first controller and with said at least one x-ray tube assembly, said second controller configured to control operating parameters of said at least one x-ray tube assembly, said parameters comprising a plurality of collision locations of electrons emitted from said at least one cathode on said at least one anode in reference to said collimator aperture; and means for controlling the directions of emitted x-ray beams.

The means for controlling the directions of emitted x-ray beams may be selected from the group consisting of at least one electromagnetic device and at least one mechanical actuator.

The means for determining the location of said at least one ROI may comprise at least one eye tracker.

The first controller may further be configured to calculate said plurality of collision locations of electrons emitted from the at least one cathode on the at least one anode according to said determined locations of said at least one ROI.

The at least one mechanical actuator may be selected from the group consisting of: electric motors, pneumatic actuators and piezoelectric actuators.

The second controller may be configured to control the means for determining said plurality of collision locations by selectively deploying at least one of: said at least one electromagnetic device and said at least one mechanical actuator. The selectively deploying may comprise deploying at least one of said at least one electromagnetic device and said at least one mechanical actuator according to the movement angles required by said at least one ROI.

The collimator may be configured to form an aperture limiting a solid angle of an x-ray beam emitted from each of said at least one anode.

The current in each of the electromagnetic devices may be set to control a direction of said solid angle of each of said x-ray beams.

The aperture may be movable in a plane generally parallel to a surface of the collimator.

The first controller may further be configured to calculate a location and size of said collimator aperture according to said determined locations of the at least one ROI.

The collimator may be movable in a plane generally perpendicular to a surface of the collimator.

The at least one cathode and at least one anode may be encapsulated in a single x-ray tube assembly.

The at least one anode may comprise a plurality of anodes.

The at least one x-ray tube assembly may comprise a plurality of x-ray tube assemblies.

The x at least one cathode may comprise a plurality of cathodes.

The plurality of cathodes and said plurality of anodes may be encapsulated in said plurality of x-ray tube assemblies wherein each x-ray tube assembly may comprise at least one anode and at least one cathode.

The processed stereoscopic image may comprise a plurality of images of the same ROI captured from a plurality of different perspectives at a plurality of different times.

The monitor may comprise a lenticular lens.

According to a fourth aspect of the present invention there is provided a method of creating a stereoscopic image captured by controlling the directions of x-ray beams emitted from at least one x-ray tube assembly via a collimator forming an aperture by manipulation of the electronic beams of said at least one x-ray tube assembly to control a plurality of collision locations of electrons emitted from at least one cathode on at least one anode, said plurality of collision locations calculated according to at least one determined ROI, comprising: determining a plurality of collision locations of electrons emitted from said at least one cathode on said at least one anode in reference to said collimator aperture; controlling the directions of emitted x-ray beams; capturing a plurality of images from a plurality of different perspectives at a plurality of different times of the same ROI; and processing said captured images to create a stereoscopic image.

The controlling the directions of emitted x-ray beams may comprise providing means selected from the group consisting of at least one electromagnetic device near the path of electrons flowing from at least one cathode to said at least one anode and at least one mechanical actuator.

The method may further comprise selecting a current level to generate a desired magnetic field in said path of the electrons flowing from said at least one cathode to said at least one anode.

The determining the location of said at least one ROI may comprise using at least one eye tracker.

The calculating said plurality of collision locations of electrons emitted from at least one cathode on the at least one anode may be done according to said determined location of said at least one ROI.

The at least one mechanical actuator may be selected from the group consisting of: electric motors, pneumatic actuators and piezoelectric actuators.

The method may further comprise selectively deploying at least one of said at least one electromagnetic device and said at least one mechanical actuator. The selectively deploying may comprise deploying according to the movement angle required by said at least one ROI.

The method may further comprise using the collimator to form an aperture limiting a solid angle of an x-ray beam emitted from the at least one x-ray tube assembly. The aperture may be movable in a plane generally parallel to a surface of the collimator.

The first controller may further be configured to calculate a location and size of said collimator aperture according to said determined location of said at least one ROI.

The collimator may be movable in a plane generally perpendicular to a surface of the collimator.

The at least one cathode and at least one anode may be encapsulated in a single x-ray tube assembly.

The at least one anode may comprise a plurality of anodes.

The at least one x-ray tube assembly may comprise a plurality of x-ray tube assemblies.

The at least one cathode and said plurality of anodes may be encapsulated in said plurality of x-ray tube assemblies, wherein each x-ray tube assembly may comprise at least one anode and at least one cathode.

The at least one cathode may comprise a plurality of cathodes.

The method may further comprise connecting each one of said plurality of cathodes to a current source; and for each one of said plurality of cathodes, selecting a heating current level to generate an electron beam in a desired electron beam current; wherein said plurality of desired electron beams currents sum up to a total desired electron beam current at the anode.

The method may further comprise displaying said stereoscopic image.

The stereoscopic image may comprise a plurality of images of the same ROI captured from a plurality of different perspectives at a plurality of different times. The stereoscopic image may be displayed on a lenticular lens.

BRIEF DESCRIPTION OF THE DRAWINGS

FIGS. 4A through 4C illustrates three examples of eye movement tracking attention monitoring devices;

FIGS. 6A-6D illustrate different embodiments for controlling the radiation source when fixation zone tracking is used;

FIG. 8 illustrates a brain activity monitoring implementation of the radiation reduction and minimization apparatus;

DETAILED DESCRIPTION OF ONE OR MORE EMBODIMENTS

The disclosure is particularly applicable to a system used to inspect/treat/diagnose a patient in which the radiation is minimized and it is in this context that the disclosure will be described. It will be appreciated, however, that the system and method for reducing radiation exposure has greater utility since it can be used in any application in which it is desirable to minimize the radiation exposure of an object or a person, such as a patient or operator, that can be harmed by that exposure and those applications may include systems that inspect an object in which the operator may be exposed to unneeded radiation (such as airports scanning systems, different security setups, manufacturing and process controls, etc.) or system to inspect a patient (such as in a clinic or a hospital, e.g. Cath lab, where a surgeon/therapist operates an X Ray or CT system, a diagnostic procedure, a treatment procedure, an imaging procedure, etc.) The radiation minimization can be used with any type of radiation including ionizing radiation sources (x-ray, gamma, alpha and beta) and non-ionizing radiation sources (electromagnetic, US). The radiation minimization may also be used with 3D systems such as CT, MRI, Bi-Plane and others.

Figure 1:
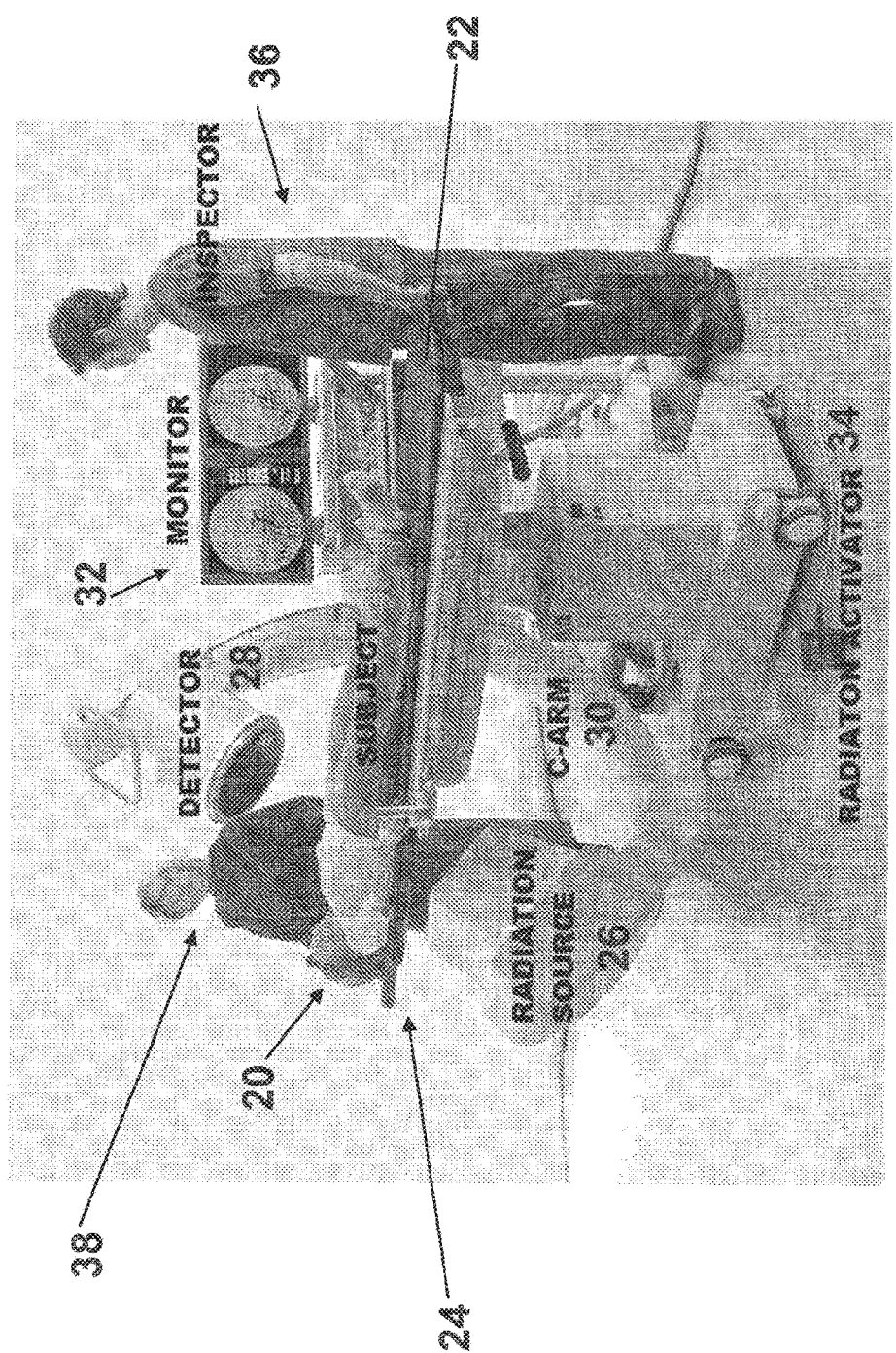
FIG. 1 illustrates an example of a medical application in which a radiation source is used to inspect a patient in which unattended radiation may occur.

FIG. 1 illustrates an example of a medical application in which a radiation source is used to inspect a patient in which unattended radiation may occur. In the medical application, a patient 20 may rest on a surface 22 of an apparatus 24. In this example, the apparatus in this example has a radiation source 26 and a detector 28 connected to each other by a C arm 30 wherein the radiation is directed at the patient 20 to image or treat a particular portion of the patient. The apparatus 24 may also include a monitor 32 on which the results of the imaging/treatment of the patient are displayed. The apparatus may also include a radiation activator 34 that allows an operate to activate the emission of radiation from the radiation source. In addition to the patient 20, there may also be an operator 36 (sometimes a physician) and an assistant 38 who are close to the apparatus 24. As a result, the patient, operator and the assistant may also be exposed to radiation and, more particularly, exposed to unattended radiation that is minimized by the radiation reduction and minimization system that is described below. The medical application shown in FIG. 1 is merely representative of the types of system that the radiation reduction and minimization system may be used for since the radiation reduction and minimization system may be used for any system in which it is desirable to be able to reduce/minimize unattended radiation, such as, but not limited to the systems identified above.

Figure 2:
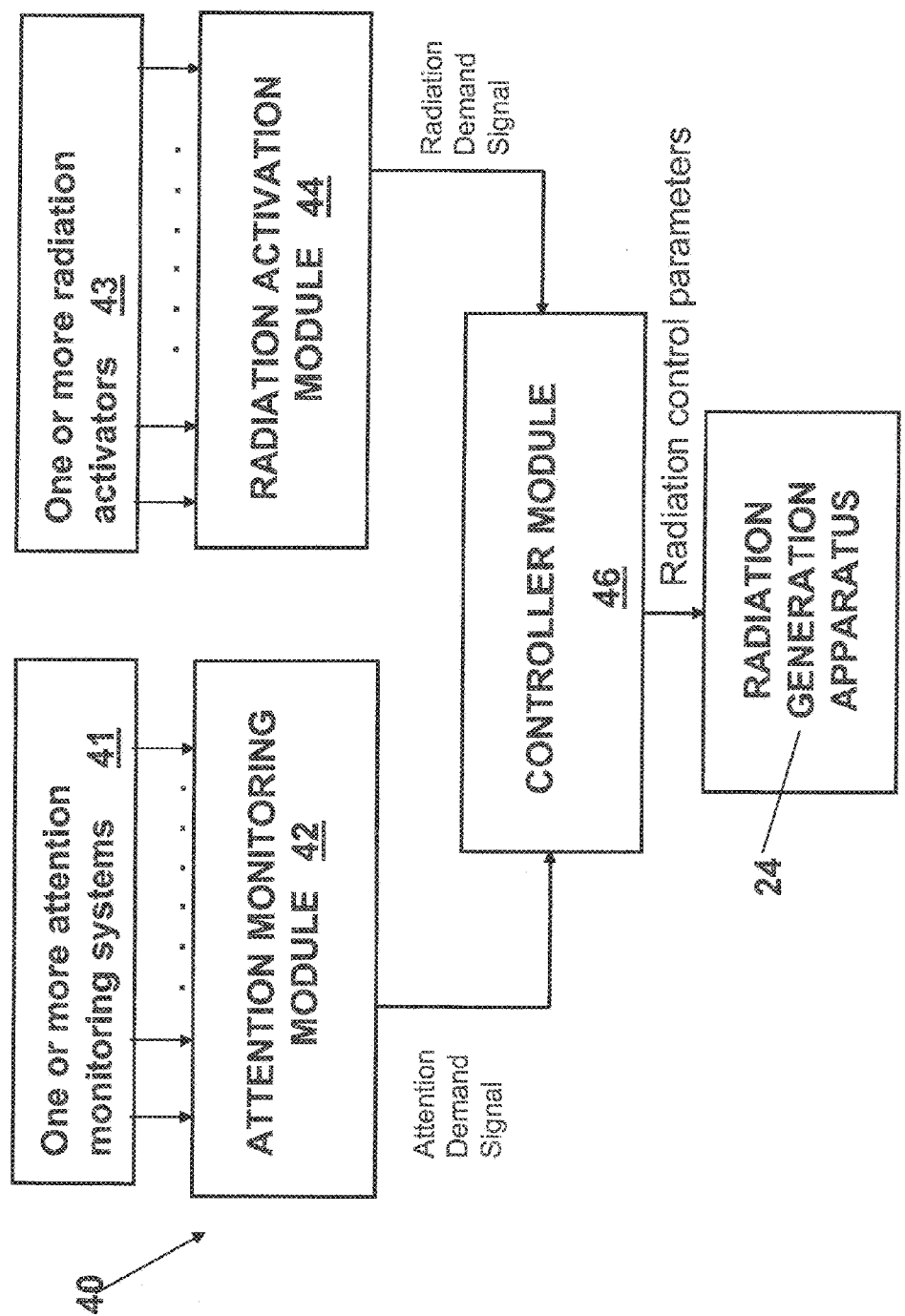
FIG. 2 illustrates an embodiment of a radiation reduction and minimization apparatus.

FIG. 2 illustrates an embodiment of a radiation reduction and minimization apparatus 40 that can be connected to a radiation generation apparatus 24 in order to reduce/minimize unattended radiation of the radiation generation apparatus 24. The apparatus 40 may be implemented as a combination of hardware elements and software elements that perform the functions and operations described below. In other implementations, the apparatus may be implemented entirely in hardware (a specially programmed hardware device or the like). The apparatus 40 may comprise an attention monitoring module/unit 42 that receives inputs from one or more operator attention monitoring systems 41, that may be implemented using a head and/or brain sensing system, an eye or eyes sensing system or a gaze sensing system that are described below, and generates an attention (e.g., gaze focus) demand signal. The attention demand signal indicates that whoever in operating the radiation generating apparatus 24 has his/her attention appropriately focused, such as directed at/towards the monitor. In more detail, the attention monitoring module/unit 42 and the controller unit 46 monitors all the users/operators to determine if and when the information generated by radiation is or may be used (e.g., the users/operators read the monitor information) and attention signal is generated. The attention demand signal is fed into a controller module/unit 46.

The operator attention monitoring systems 41 may alternatively include an image analysis and automated identification of a region of interest system. For example, the system can automatically identify the location of a tip of a catheter using well-known image processing techniques (for example identifying the motion of the device that is inside the body, a predetermined geometric shape of the device and/or a specially marked device) and the direction of the radiation towards this location in order to identify that the operator is alert since the catheter should be at the same location as the radiation. The device being guided (such as the catheter tip) also can be "marked" with a special indicator. This may be accomplished in several ways including a built in software which performs proper image segmentation and object (say tool/catheter) recognition, followed by reference/access to a pre-loaded medical procedure knowledge (data) base, which will provide the coordinate for the focused radiation (region of high interest). This image analysis and automated identification of a region of interest system can be used with the other attention monitoring systems described above or can be used instead of the attention monitoring systems described above.

The apparatus 40 further may comprise a radiation activation module/unit 44 that receives inputs from one or more radiation activation devices 43, such as the radiation activator 34 in FIG. 1 or any other device that indicate an intent by the operator/assistant to activate the radiation source, and generates a radiation demand signal. The radiation demand signal indicates that the operator has activated the radiation activation devices (indicating intent by the operator/user to initiate radiation) indicating that radiation should be generated. The radiation activation devices may implemented in a variety of ways including a pedal (as shown in FIG. 1), a mechanical switch; a voice command, an optical designation as well as many others that are all can be used with the radiation minimization apparatus since the radiation minimization apparatus is not limited to any particular radiation activation devices. If the radiation activated device has been activated, the radiation demand signal is also fed into the controller module/unit 46.

The controller module/unit 46, based on the radiation demand signal and attention demand signal inputs, activates the radiation generating apparatus in such as way as to reduce/minimize unattended radiation. In particular, the radiation demand signal and the attention demand signal must indicate that the operator's attention is appropriately focused and that the radiation activation device has been activated by the operator. Since both signals must be present in order to activate the radiation generation apparatus, unattended radiation exposure is reduced/minimized. In particular, when the radiation activation device is activated, but the operator's attention is not appropriately focused (based on brain activity monitor and/or detection of the optical focusing by the eye tracking device), it is likely that the operator is not paying attention so no or minimal level (to be determined by the user) radiation is generated by the radiation generation apparatus. Similarly, if the operator's attention is appropriately focused, but the radiation activation device is not activated, the operator likely does not want radiation to be generated so no radiation is generated by the radiation generation apparatus. Thus, the controller module/unit 46 only enables the onset of radiation (using appropriate handshaking and control interface) when both the attention monitoring module and the radiation activation module send an ON signal.

The controller module/unit 46 may also control other aspects of the diagnostic/treatment system. In particular, the controller module/unit 46 may control the patient table 22 based on the attention of the operator. In typical system, most of the time a physician would like to have the center of his attention in the middle/center of the screen/monitor and the physician frequently manually repositions the table and the x-ray tube to achieve it in a typical system. Using the system described herein, the physician, when he/she decided that he/she wants to reposition the table, he/she sends command to the system to adjust table/x-ray tube position to their attention (for example based on their gaze location) and the system can automatically adjust the table. The physician command can be executed by either voice or switch. The operator will have an over-ride switch to turn this option on or off.

When radiation is to be generated by the radiation generation apparatus 24, the controller module/unit 46 may generate one or more radiation control parameters that are used to control the generation of the radiation by the radiation generation apparatus 24. The one or more radiation control parameters may include a location of the radiation (when it is desirable to narrowly focus the radiation on a particular location), filtering/collimating of the radiation outside the center of the attention, timing (the time that the radiation will be generated), frequency (the number of times over a predetermined amount of time that a pulsed radiation beam is generated) and intensity (for radiation generating apparatus in which the intensity of the radiation beam may be adjusted). For example, for an xray, kVP as the energy of the beam is used and mA-density for the intensity of the beam. The parameters may also include the amount of collimation/filtering of the radiation to restrict the beam to the point of attention. Other parameters of importance are the spatial and temporal rates of reduction from the center point with high radiation towards the periphery of the image where smaller (or no) level of radiation may be required.

In configurations with multiple radiation sources aimed at the same target (patient/object), the radiation parameters may also include an identifier of the radiation source to be used (sometimes at different times). Using these one or more radiation control parameters, the controller module/unit 46 can further minimize unnecessary radiation by ensuring that only the necessary amount of radiation for the particular task is used by controlling elements of the radiation generation apparatus such as the electronic grid, filtering, collimation, etc. The one or more radiation control parameters also can be used to ensure that radiation is only directed at a particular location when a particular location can be identified which reduces extraneous radiation on locations that do not need to be irradiated. In addition, the unattended radiation can be blocked using an electrical grid of the radiation source or by placing a shield that blocks the radiation. Now, several examples of situations in which unattended radiation can occur are described, including: 1) a no look, no radiation situation; 2) a "if you cannot use it, do not ask for it" situation; 3) a "where you see if where you get it" situation; and 4) "if you really want it, you will get it" situation.

No Look—No Radiation Situation

In this situation, the operator continues to operate the radiation generating apparatus source while not even looking at the monitor or without his/her attention appropriately focused. The radiation reduction and minimization apparatus described above may be used to remedy this situation in which an operator gaze/look monitoring system is synchronized with a radiation activation device to turn off the radiation generating apparatus if and when the designated operator is not looking at the screen to reduce the radiation exposure of the patient (in medical applications) and/or the operator and other people adjacent the radiation generating apparatus during the operation of the radiation generating apparatus.

In this situation, the attention monitoring devices 41 may be implemented in several different ways. The first implementation of the attention monitoring devices 41 may be a gaze tracking device. The gaze tracking device may be a device that is already commercially available or a customized gaze tracking device and the radiation reduction and minimization apparatus may be used with various types of gaze tracking devices. For example, the gaze tracking devices may include various commercially available eye tracking systems such as those made by SensoMotoric Instruments Inc. (www.smivision.com) and system that can be found at www.sr-reasearch.com/index.html).

Figure 3:
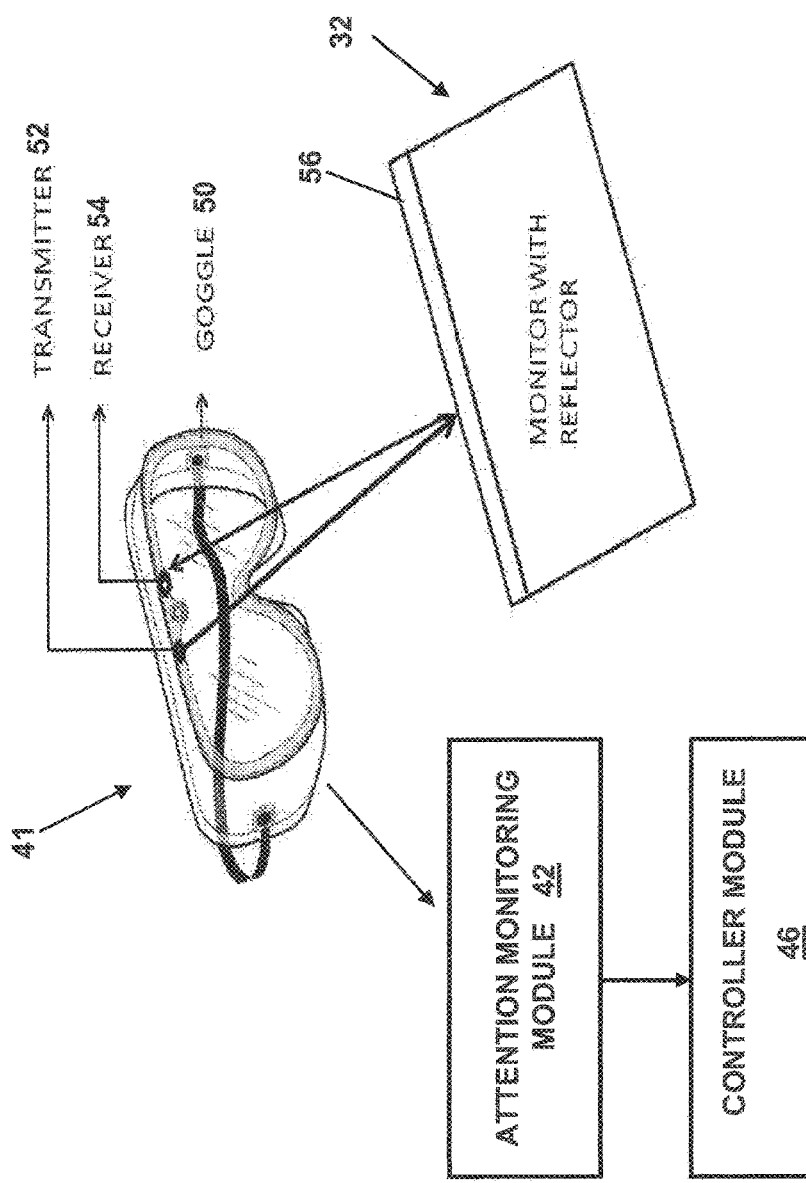
FIG. 3 illustrates an example of a gaze direction monitoring device that can be used with the radiation reduction and minimization apparatus.

Another implementation of the attention monitoring devices 41 may be gaze direction monitoring systems that determine if the operator's gaze is appropriately directed, such as at a monitor. An example of a gaze direction monitoring device that can be used with the radiation reduction and minimization apparatus to remedy this situation is shown in FIG. 3. The radiation reduction and minimization apparatus has the same modules/units shown in FIG. 2 (although not all of the modules/units are shown in FIG. 3). The gaze tracking device in FIG. 3 has a set of goggles/glasses 50 that have a set of sensors and a transmitter/emitter 52 and a set of sensors and a receiver 54 and a reflector 56 on the monitor 32. Alternatively, the transmitter and/or receiver may be attached to the head of the operator. The transmitter sends an electromagnetic energy beam (infrared, radio frequency, laser, etc.) towards the reflector 56 and the reflected energy is received by the receiver 54 to determine if the gaze direction of the operator is towards the monitor 32. When the operator is not gazing at the monitor 32, the energy from the transmitter is not reflected (or the reflected signal does not have a particular characteristic) so that it is determined that the operator is not gazing at the monitor. In this embodiment of the gaze direction monitoring devices, several designs of the emitter-receiver combination may be used including, but not limited to: 1) an emitter and receiver at the visual target and the reflector at the head of the operator; 2) an emitter on the target and the receiver located at the head of the operator; 3) an emitter and receiver at the head of the operator; 4) an emitter at the head of the operator and the receiver on the target; 5) either emitter or receiver or both are located elsewhere in the operational site; 6) silhouette monitoring with regular light or an infrared camera; and 7) three dimensional (3D) image monitoring in which the position of the head will be recorded and the cameras are located on the monitor and can recognize the face and expression of the operator including direction the gaze.

In this situation, the radiation activation module/unit 44 has the same elements and operation as described above in FIG. 2. The controller module/unit 46 also has the same elements and operation as described above in FIG. 2. In this situation, the apparatus prevents radiation exposure when the operator is not appropriately focused or looking at/towards the monitor 32.

An example of this situation occurs in a catheterization lab. In particular, live/continuous fluoroscopy is routinely used to perform minimally invasive surgical procedures in order to facilitate the navigation inside the human body. Guided by the live/continuous fluoroscopy and using the small radiopaque (visible under x-ray) equipment (catheters, balloons, stents, coils), the operator can navigate inside the human body and deliver the treatment to the specific location. Typically, the radiation source is activated by the user/operator, commonly by switch/foot pedal, which activates the radiation source (x-ray tube), which in turn generates the x-rays. The x-rays then pass the object/patient and the detector camera receives the information. The information is then presented on the monitor for the analysis by the user/operator. In many cases these surgical procedures demand significant mental concentration and attention to the details. In these cases the operator can be distracted by the complexity of the procedure and continues to operate x-ray equipment while not looking at the monitor. This results in "unnecessary" radiation that doesn't provide the information to the operator, significantly increasing the radiation dose that is harmful to the patient and to the operator. The radiation reduction/minimization systems reduces this unnecessary radiation.

"If You Cannot Use it—do not Ask for it" Situation

During some phases of human visual processing, there are phases or time segments, such as the saccades (physiological eyes movements which occurs several times every second and last about 80 Millisecond each, or during "Perclose" (times when the eye lids are temporarily closed) where the brain doesn't acquire/process/exploit the visual information "landing" on the retinae (saccade masking) and useful visual information is only extracted during eye fixations phases. In this situation, a radiation minimization apparatus is used that has an operator saccade detector (the attention monitoring device 41 in this situation) synchronized with a radiation activation device). The radiation minimization apparatus turns off the radiation source during such "wasteful" time segments (such as "saccade masking"). One popular way to deliver the radiation is what is called "pulsed fluoroscopy" in which a pulse rate of 30 pulses per second is used. Using the radiation minimization apparatus, the pulses that are fall within the "wasteful" time segments (saccade masking and perclose) will be blocked.

In this situation, the attention/eye tracking monitoring devices 41 detects the phase of the operator visual path and, during the "inattentive" phases of the visual cycle, this module sends of signal to the controller module to block the radiation. The attention monitoring devices 41 may be implemented in several different ways. The first implementation may be gaze/eye tracking technology as described above. In another implementation, the attention monitoring devices 41 may be eyeball tracking technology (with three examples shown in FIGS. 4A through 4C). The eyeball tracking technology may be head or headband mounted version (FIG. 4A), a goggle mounted version (FIG. 4B) or a remote version (FIG. 4C) in which one or more sensors 406 (such as piezoelectric, magnetic, capacitive, IR, video or laser sensors, for example) are mounted to detect the eye movement of the operator. In specific implementations, the eyeball tracking technology may be an infrared cameras located in the radiation protection goggles, one or more capacity sensors located in the radiation protection goggles, one or more optical cameras located in the radiation protection goggles, laser emitter-receiver combination or Us sensors.

In this situation, the radiation activation module/unit 44 has the same elements and operation as described above in FIG. 2. The controller module/unit 46 also has the same elements and operation as described above in FIG. 2. In this situation, the apparatus prevents radiation exposure when the operator is not appropriately focused or looking at/towards the monitor 32.

"Where You See it is where You Get it" Situation

Figure 5A:
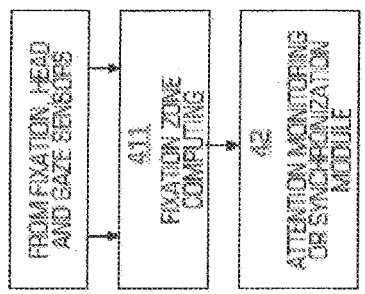
FIGS. 5A and 5B illustrates a fixation zone tracking implementation of the radiation reduction and minimization apparatus.
Figure 5B:
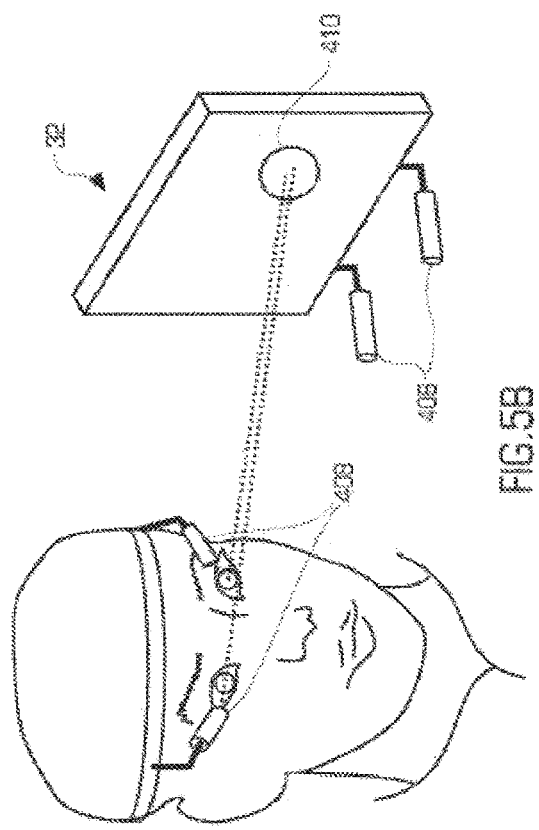

In many online procedures involving visual monitoring, most of the time the fixation zone of the operator is engaged with procedure details (e.g., a device, tool edge, anatomic feature etc.) of dimensions/sizes which are usually a small fraction (e.g., 1 to 5%) of the full imaged area (field of view (FOV)) [16 inch]. The image data surrounding this fixation zone, although useful for contextual information do not require the same refresh rate (frequency of radiation) nor the intensity and resolution needed within the fixation zone. Furthermore, even if provided, the operator doesn't fully perceive nor exploits the information outside this area of the highest visual and mental concentration (the fixation zone). In this situation, in order to reduce the radiation dose, the radiation is optimized by optimizing the radiation parameters (frequency, intensity, temporal and spatial resolutions) for each zone of the FOV on the basis of the utility of the information. An optimization process in the controller module 46 computes the proper parameters for each image segment. For example, in a simplistic embodiment of the process, the fixation zone receives high radiation frequency and high intensity of radiation and all other zones (background image) receive minimal (low) radiation or even no radiation, deploying past history images and avoid refresh altogether. In this situation, as depicted in FIGS. 5A and 5B, an operator fixation zone monitor 32 is synchronized (via controller module) with a radiation activation device. In this situation, the fixation sensors 408 are used to determine a fixation zone 410 of the operator on the monitor 32. The fixation sensors 408 operate is the same manner as the eye tracking since the eye tracking is based on the recording of the movement and location of the pupils that gives both gaze direction, eye movement and gaze/attention location. In this situation, the attention monitoring module includes a fixation zone determining module 411 that determine the fixation zone of the operator. In this situation, the attention monitoring devices may use similar attention monitoring devices as described above.

Figure 6A:
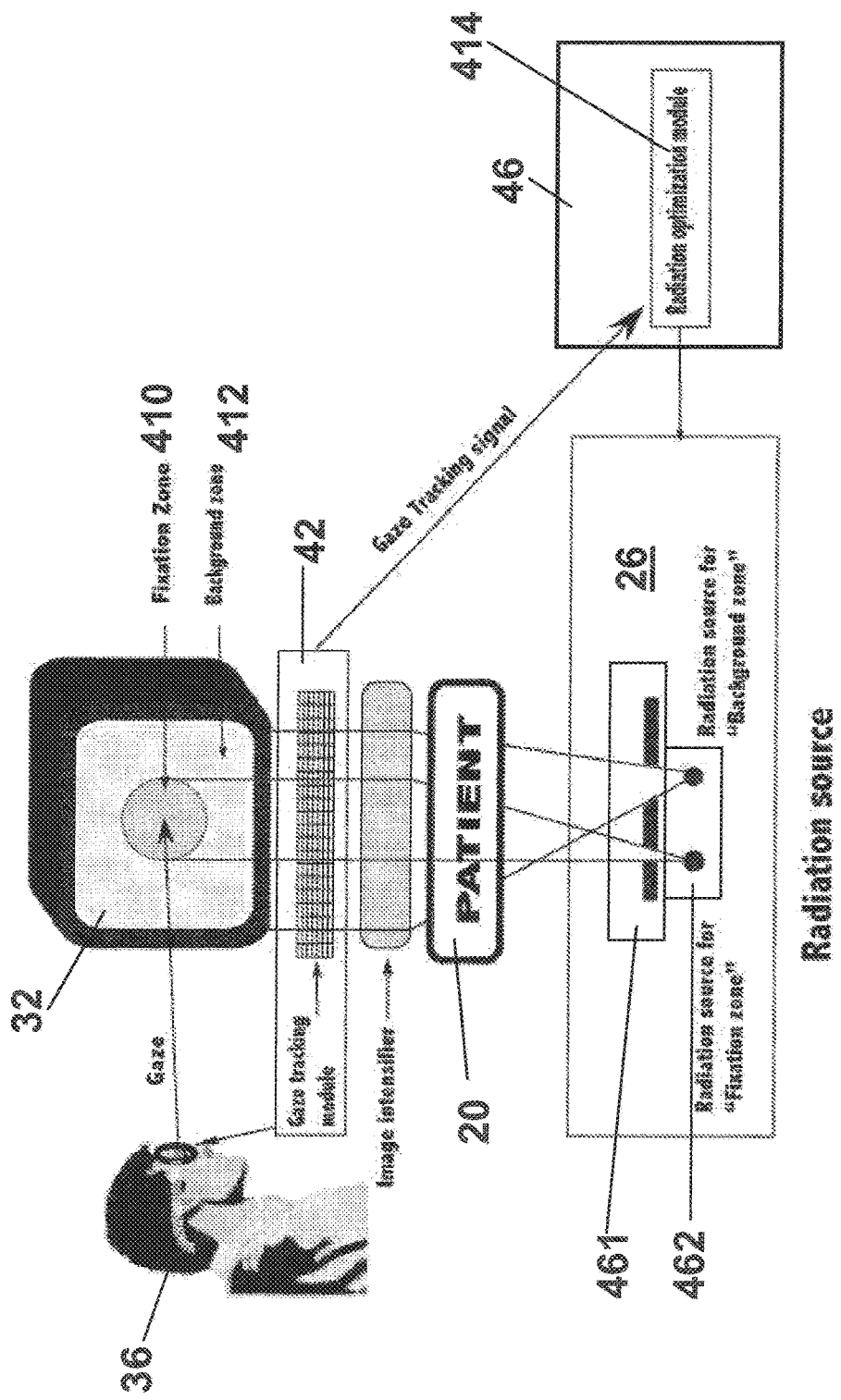
Figure 6B:
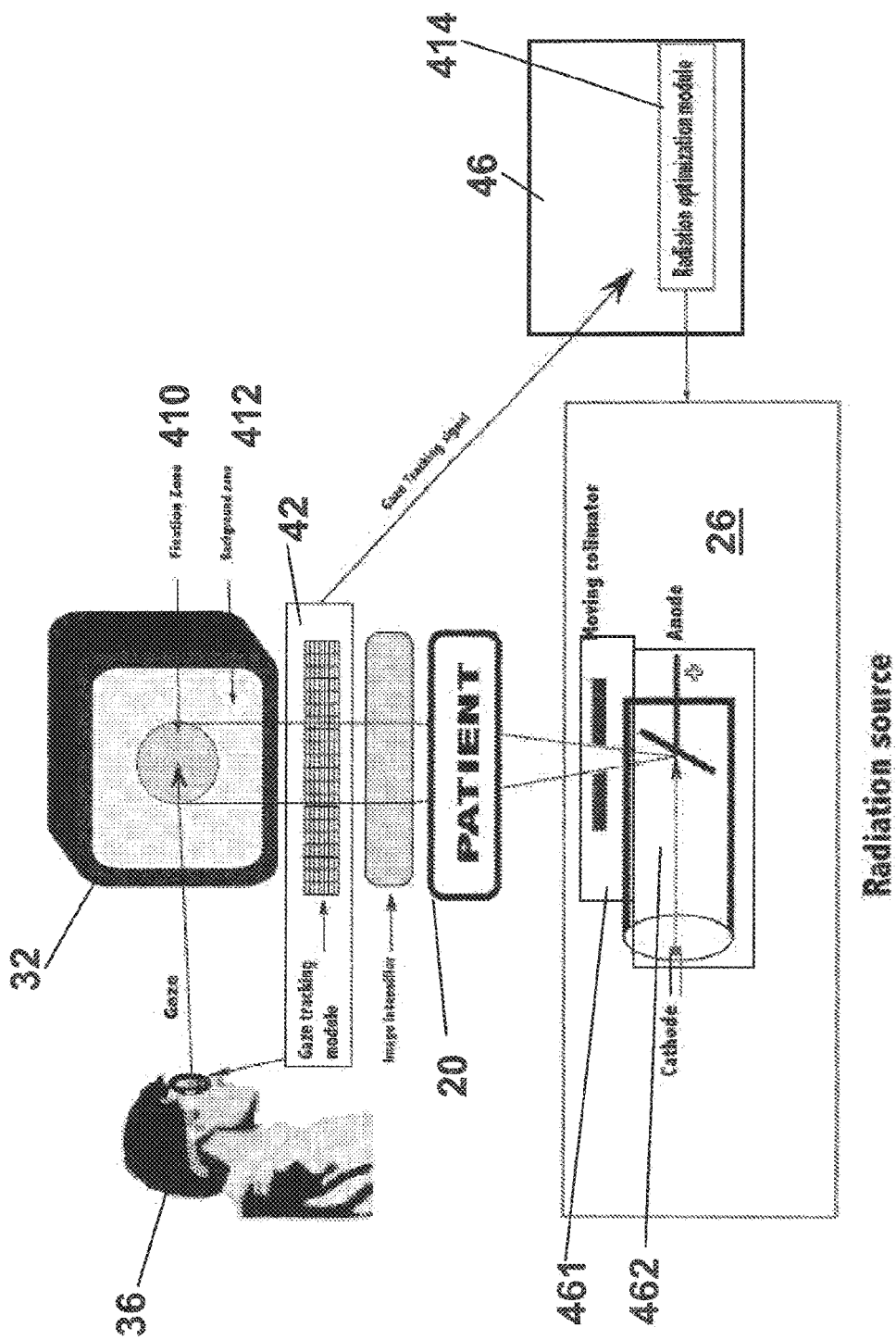
Figure 6D:
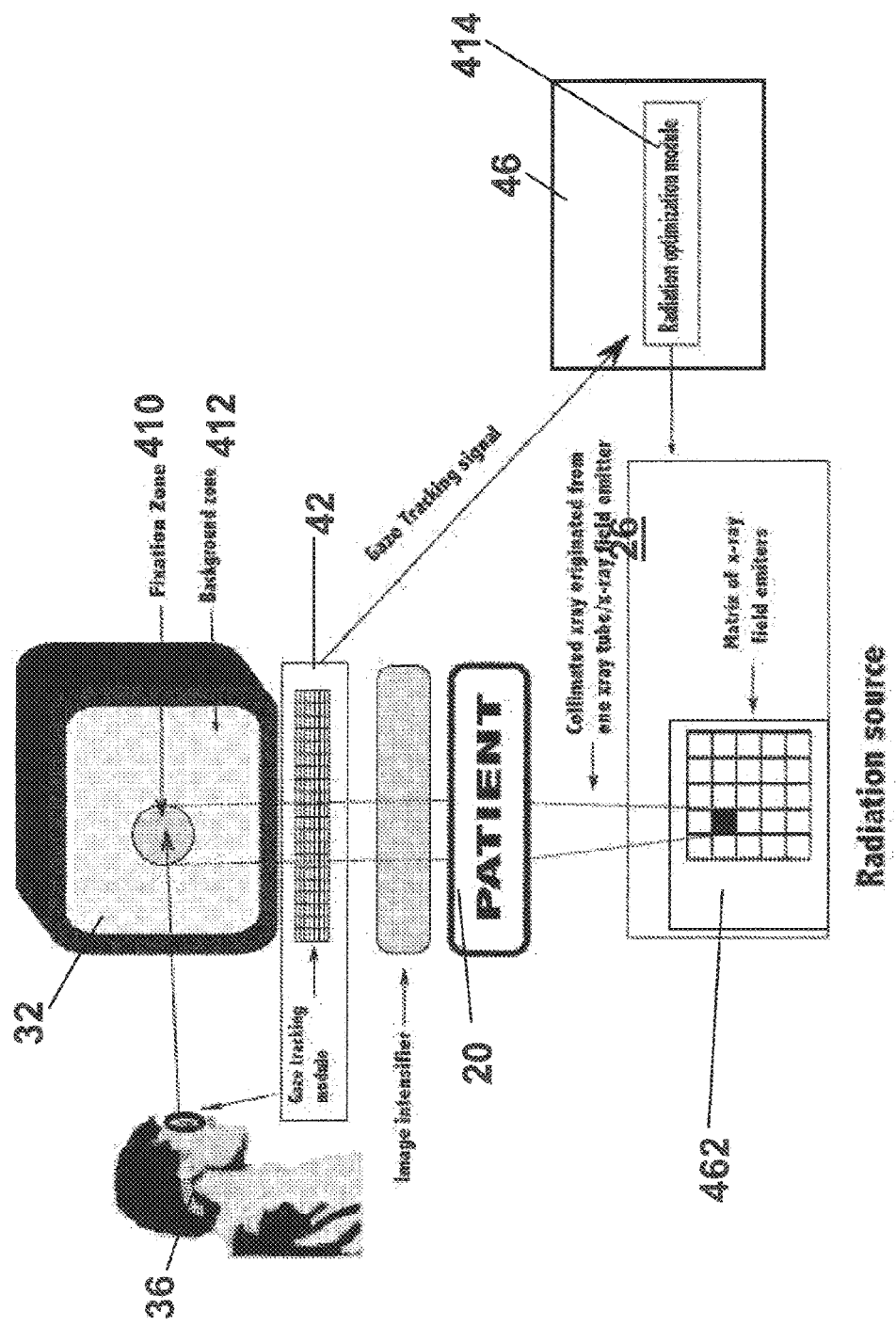

In this situation, the radiation activation module/unit 44 has the same elements and operation as described above in FIG. 2. For the controller module/unit 46 and the radiation source 26, several different embodiments are shown in FIGS. 6A-6C.

Figure 7:
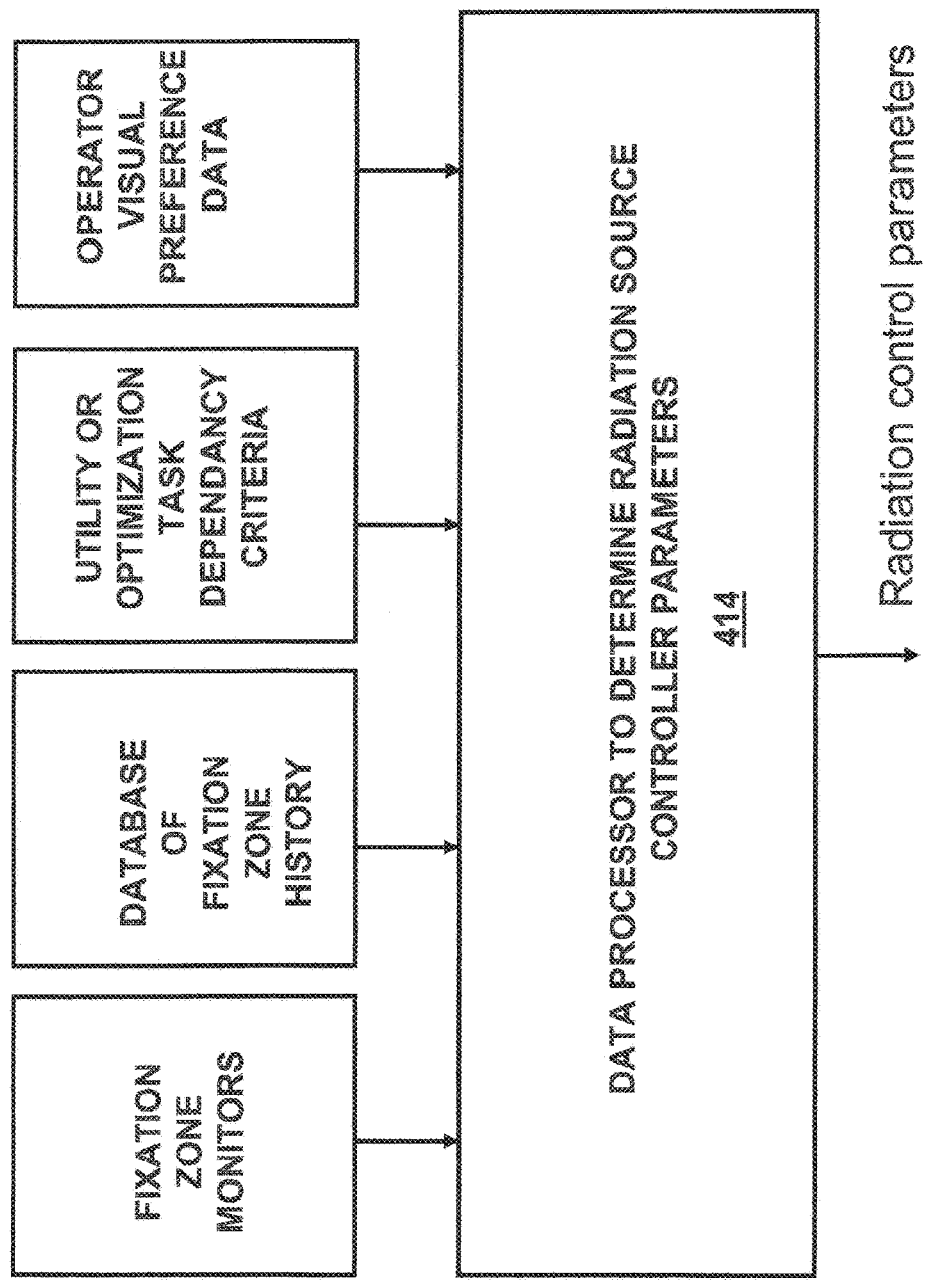
FIG. 7 illustrates more details of the controller module for fixation zone tracking.

The controller module 46 has a radiation optimization module 414 in each of the embodiments. The radiation optimization module 414 computes in real time (using the gaze tracking signal) and delivers to the radiation source controller, the optimal radiation parameters (pulse rate, intensity (mAm), energy (Kvp) of the radiation beam and resolution needed per each image segment within the entire FOV). This module may be using an optimization process which is using the archived history of fixation zones and their timing as tracked by the eyes as well as the radiated profiles and their timing as delivered for each image zone as shown in more detail in FIG. 7. The module allocates the minimal dosage necessary within each (pixel) image segment subset which is needed in order to deliver the necessary image clarity and validity (timing) to the operator. For example it will initially receive the information regarding the area of maximal attention of the FOV (the gaze tracking signal) from the attention monitoring module 42 as shown in FIG. 6A-6C. This area will be designated by the radiation optimization module 414 to receive significantly more radiation in terms of increased mAm and pulse rate than the rest of FOV in order to provide optimal imaging. This will result in much better temporal, contrast and spatial resolution that in term will improve the operator performance. The radiation profile and radiation parameters are then transferred the radiation source 26.

The radiation source 26, for this situation, is designed so that the radiation source can deliver different radiation doses to the different segments of the FOV. Generally, this can be achieved using either mechanical or electronic collimators, electron beam radiation source or combination of several radiation sources. In one implementation, the radiation source 26 may be a standard radiation source, such as an x-ray tube, with moving mechanical collimator or region of interest (ROI) filter so that the mechanical collimators (or filters) 461 as shown in FIG. 6A can be used dynamically expose the areas of maximal attention 410 and collimate the rest areas of FOV 412. In another implementation, two or more radiation sources 462, such as an x-ray tubes, as shown in FIG. 6A may be used in which the several radiation sources provide the radiation for the area of maximal attention and the others for the rest of FOV with corresponding collimators arrangements. In yet another implementation of the radiation source, the radiation source may have a anode/cathode 462 as shown in FIG. 6B and a moving collimator (or ROI filter) 461 that is used to adjust the radiation directed towards the fixation zone 410 and towards the background zone 412.

In yet another implementation, the radiation source may have a collimator (or ROI filter) 461 and a anode with a complex geometry 462. In this implementation, the radiation source are designed the way similar to the Electron beam CT (see for example U.S. Pat. No. 4,352,021) in which the electrons that originate at the cathode are directed by an external magnetic field toward different segments/parts of the anode or to the different anode targets. The anode is designed as a complex array of geometrically oriented targets (for example, a matrix of the targets). The anode also can be mechanically moved in order to change the angle and thus create an additional option for moving the radiation beam. The application/direction of the electron beam to the different parts of the anode result in the change in the direction of the radiation. The direction of the radiation will then correlate with the area of maximal attention. The radiation of the rest FOV will be provided either by different xray tube or different electron beam source in the same x ray tube.

In yet another implementation, the radiation source may have matrix of radiation field emitters 462 (or small conventional radiation tubes that are commercially available.) The electron field emission are attractive way to extract free electrons because the electrons are emitted at room temperature and the output current is voltage controllable. Recently the researchers from the UNC optimized the morphology of carbon nanotubes (CNT) films that optimize the electrons current for the xray generators (See U.S. Pat. No. 7,085,351 b2). In this scenario the non uniform radiation can be activated (or the changing of the radiation parameters) using different combination of the radiation field emitters. The x-rays that are generated using CNT are high frequency and high intensity and more programmable. The xray source can be designed as a square matrix of the multiple field emission xray tubes or conventional radiation tubes. In this design the each xray tube is separately programmable and can deliver the xray beam of desired intensity to the specific area. For example one of the xray tubes will deliver the maximum radiation dose to the maximum attention area 410 and the others deliver lower radiation dose to the rest of the field of view 412.

The matrix of radiation, such as x-ray, tubes also can be extended to resemble a partial CT scanner. In this case, it is possible to create a 3D or CT type of images and the generation of CT images during fluoroscopy guided interventional procedures is a very desirable feature for the surgeon. However, the continuous CT type of scanning of the whole body subjects the patient to a large amount of radiation. Using the radiation minimization and reduction apparatus above with the attention monitoring, the CT type of scanning of the whole body can be performed in the specific fixation zones 410 and the images are intermittently generated so that the radiation exposure is reduced.

"If You Really want it, You Will Get it" Situation

In many situations an operator may be looking, even fixating steadily at an image subzone—yet his/her "mind" drifts off "thinking/engaging" in mental activities which are not directly related to the task at hand. Brain monitoring technology 800 may be used which when deployed will allow for setting off an alert signal whenever the operator switches his/her attention/focus from the current task. In this situation, the operator attention focusing/brain state monitor 800 and the fixation zone monitor 42 are synchronized as shown in FIG. 8.

The mental attention monitoring module 800 may be a module, such as the electrodes and the brain state monitor shown in FIG. 8, so that mental attention can be monitored using the ECG electrodes (see for example, U.S. patent application Ser. No. 11/145,612 that lists Bruce Katz and Allon Guez as inventors that is titled "Brain State Recordation System", the entirety of which is incorporated herein by reference. In this situation, the radiation activation module and controller module have the same elements and operation as described herein.

Figure 9A:
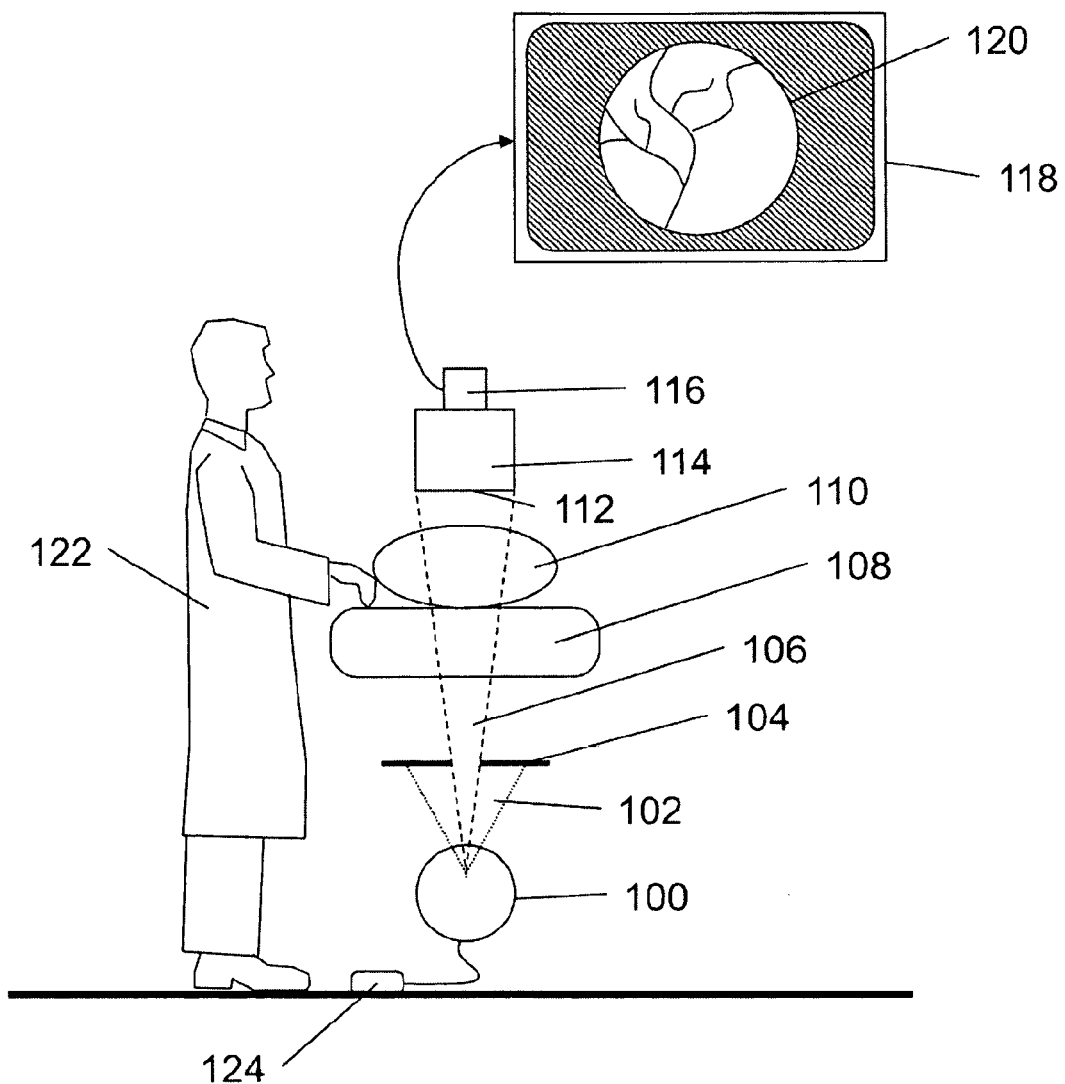
FIG. 9A is a schematic drawing of a typical layout of a fluoroscopy clinical environment.
Figure 9B:
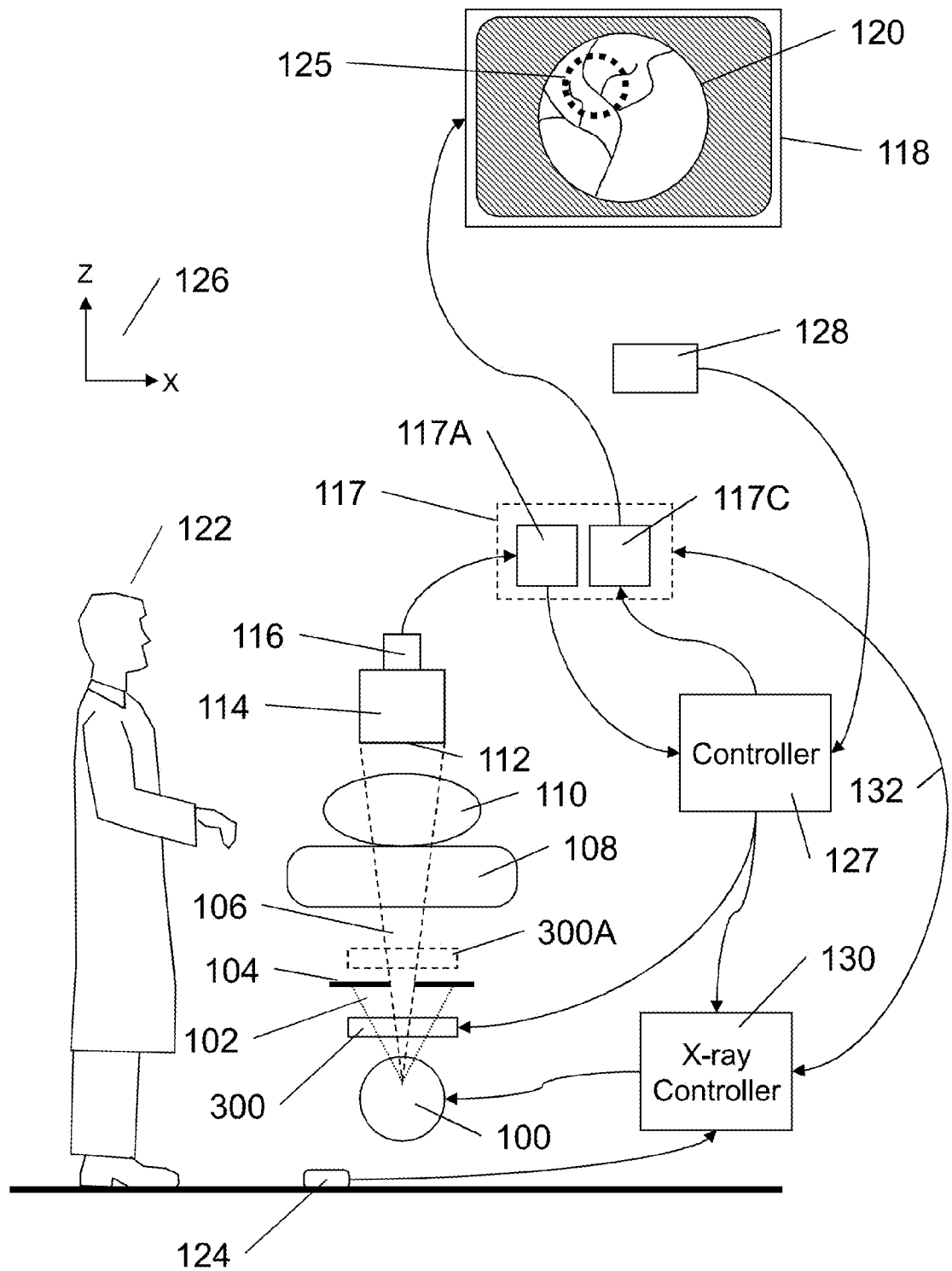
FIG. 9B is an illustration of an example of a layout of the system of FIG. 9A showing additional details of components of the system example of the invention.

The present invention provides means for attaining high exposure at the input area of the image intensifier in the desired Region of Interest (ROI) that will provide therefore a high S/N image there while reducing the exposure of other sections of the image intensifier area, at the cost of lower image quality (lower S/N). With this arrangement the operator can see a clear image in the ROI and get a good enough image for general orientation in the rest of the image area. ROI 125 location example in image area 120 as shown in FIG. 9B can be determined by any mean such as, but not limited to, pointing by a mouse at the desired center position of the ROI, using a track-ball to move ROI over image 120 area, typing-in image coordinates for ROI center, using input from an eye tracker to place the ROI at the gazing point of the user, etc.

One such example according to the present invention is presented hereinbelow in more details in reference to FIG. 9B.

Operator 122 presses foot switch 124 to activate x-ray. Eye tracker 128 (such as EyeLink 1000 available from SR Research Ltd., Kanata, Ontario, Canada) or any alternative input device provides indication where operator 122 is looking. This information is typically provided relative to monitor 118. This information, the "gazing point", may be provided for example in terms of (X,Z) coordinates, in the plane of monitor 118, using coordinate system 126. It would be appreciated that in this example the plane of monitor 118 and therefore also image 120 are parallel to the (X,Z) plane of coordinate system 126. Other coordinate systems are possible, including coordinate systems that are bundled to monitor 118 and rotate with monitor 118 when it is rotated relative to coordinate system 126. The data from input 128 is provided to controller 127 which is basically a computer, such as any PC computer. If the controller 127 determines that the operator's gaze is not fixed on the image 120, the x-ray tube 100 is not activated. Otherwise x-ray tube 100 is activated and x-ray radiation is emitted towards collimator 104 (and 300/300A if they are included in the system as will be explained in reference to FIGS. 11, 12, 13 and 14).

Box 300 can be located under collimator 104 or above collimator 104 as shown by numerical reference 300A. The collimators represented by boxes 300 and 300A are controlled by controller 127. X-ray emission is also controlled by controller 127, typically through x-ray controller 130. In one example, x-ray can be stopped even if operator 122 presses foot-switch 124, if the operator's gazing point is not within image 120 area. Also the location of focal point 304 (shown in FIG. 11) is controlled according to the location of ROI 125 through controller 127 as explained, for example, in reference to FIGS. 11 and 12. The collimator partially blocks radiation, depending on the determined operator's gazing point (or other ROI position input method) and thus part of the x-rays are absorbed by patient 110 and the remaining radiation arrives at image intensifier 114. The image is captured by a camera 116 and is transferred to image processor 117. Processed image 120 is displayed on monitor 118.

Image processor 117 may assume many forms and may be incorporated in the current invention in different ways. In the example of FIG. 9B, image processor 117 includes two main sub units: 117A provides basic image correction such as pixel non-uniformity (dark offset, sensitivity, reconstruction of dead pixels etc), 117C provides image enhancement processing (such as noise reduction, un-sharp masking, gamma correction etc). In conventional systems, the image from sub-unit 117A is transferred for further processing in sub-unit 117C. The sub-units of image processor 117 can be supported each by a dedicated hardware but they can also be logical sub-units that are supported by any hardware.

In the example of FIG. 9B the image from camera 116 is corrected by image processing sub-unit 117A and then transferred to controller 127. Controller 127 processes the image as required from using any of the collimators represented by box 300 and 300A and/or from moving focal point 304 (FIG. 11) to compensate for non-uniform exposure of image 120 area and returns the processed image to sub-unit 117C for image enhancement.

It can be appreciated that the image processing of controller 127 does not have to take place in controller 127 and it can be executed by a third sub-unit 117B (not shown in FIG. 9B) located between 117A and 117C. Sub-unit 117B can also be only a logical unit performed anywhere in image processor 117.

It would also be appreciated that x-ray controller 130 is presented here in the broad sense of system controller. As such it may also communicate with image processor 117 to determine its operating parameters and receive information as shown by communication line 132, It may control image intensifier 114, for example for zoom parameters (communication line not shown), it may control camera 116 parameters (communication line not shown), it may control the c-arm and bed position (communication line not shown) and it may control x-ray tube 100 and collimator 104 operation parameters (communication line not shown). There may be a user interface for operator 122 or other staff members to input requests or any other needs to x-ray controller 130 (not shown).

Physically, part or all of image processor 117, controller 127 and x-ray generator (the electrical unit that drives x-ray tube 100) may all be included in x-ray controller 130. X-ray controller 130 may contain one or more computers and suitable software to support the required functionality. An example for such a system with an x-ray controller is mobile c-arm OEC 9900 Elite available from GE OEC Medical Systems, Inc., Salt Lake City, Utah USA. It would be appreciated that the example system is not identical to the system of FIG. 9B and is only provided as a general example.

Figure 10A:
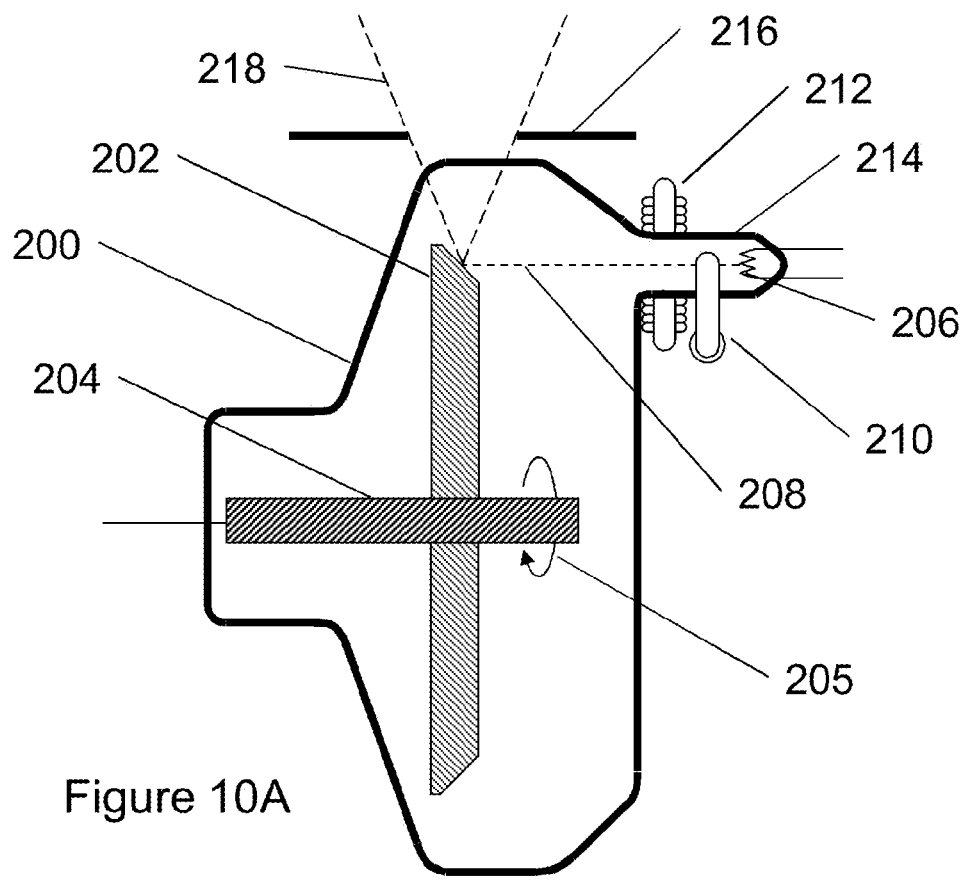
FIG. 10A illustrates a schematic x-ray tube with deflection yokes including ferromagnetic cores.

Reference is made now to FIG. 10A illustrating a schematic x-ray tube with deflection yokes comprising ferromagnetic cores.

Encapsulation 200 enables the vacuum required to enable electron beam 208. A cross section of anode 202 is shown. Anode 202 is a typical rotation anode that rotates about axis 204 (cross section is shown) as illustrated by arrow 205. Cathode 206 emits electron beam 208 that is focused on anode 202. Deflection yokes 210 and 212 are arranged generally perpendicular to each other on cylindrical section 214 of the x-ray tube encapsulation 200, as will be explained in more details in FIG. 10B. X-ray radiation resulting from the collision of the electrons of electron beam 208 with anode 202 is radiating in a relatively broad solid angle that is then limited by collimator 216 to produce the limited solid angle 218. The typical geometry, with a round collimator opening in the case of a round image intensifier input area, will produce a conical x-ray beam that spreads out towards the image intensifier. When reaching the image intensifier input area the diameter of the beam is generally the same as the diameter of the image intensifier input area. This enable the full utilization of the image intensifier input area but, at the same time, the ROI that may be in the order of 50 mm in diameter and the rest of input area 112 of FIG. 9A are exposed with a similar radiation regardless of the distinguishable value for the operator of the two sections.

Figure 10B:
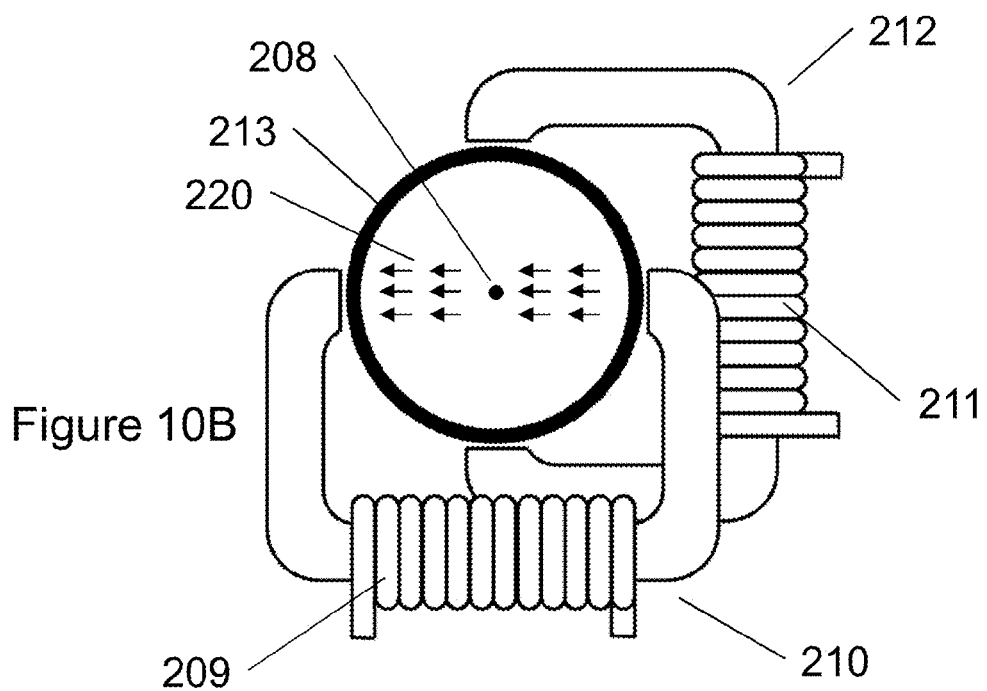
FIG. 10B illustrates a more detailed view of an arrangement of the deflection yokes of FIG. 10A.

Reference is made now to FIG. 10B illustrating the arrangement of yokes 210 and 212 in more details.

213 is a cross section of the cylindrical element of encapsulation 200 described in references to FIG. 10A. 208 is the electron beam of FIG. 10A shown in a cross section view of the electron beam. The electrons propagate into the page. At rest, no current is driven through coil 209 of yoke 210 and coil 211 of yoke 212.

Now, if electrical DC current is introduced through coil 209, a horizontal magnetic field is generated in the space where the electrons of electron beam 208 are traveling. This is demonstrated by magnetic field arrows 220. As a result of magnetic field 220 the electrons in electron beam 208 sense electromagnetic force downwards and move in this direction. As a result, electron beam 208 will collide with the anode 202 at a lower point compared to the situation of no electrical current in coil 209. Similarly electron beam 208 can be deflected upwards by introducing to coil 209 an electrical current in the other direction. The amount of vertical deflection of electron beam 208 depends on the magnitude and the direction of the electrical current in coil 209.

In a similar way, by controlling the electrical current through coil 211 a vertical magnetic field can be manipulated to deflect electron beam 208 in the horizontal direction as desired.

Figure 10C:
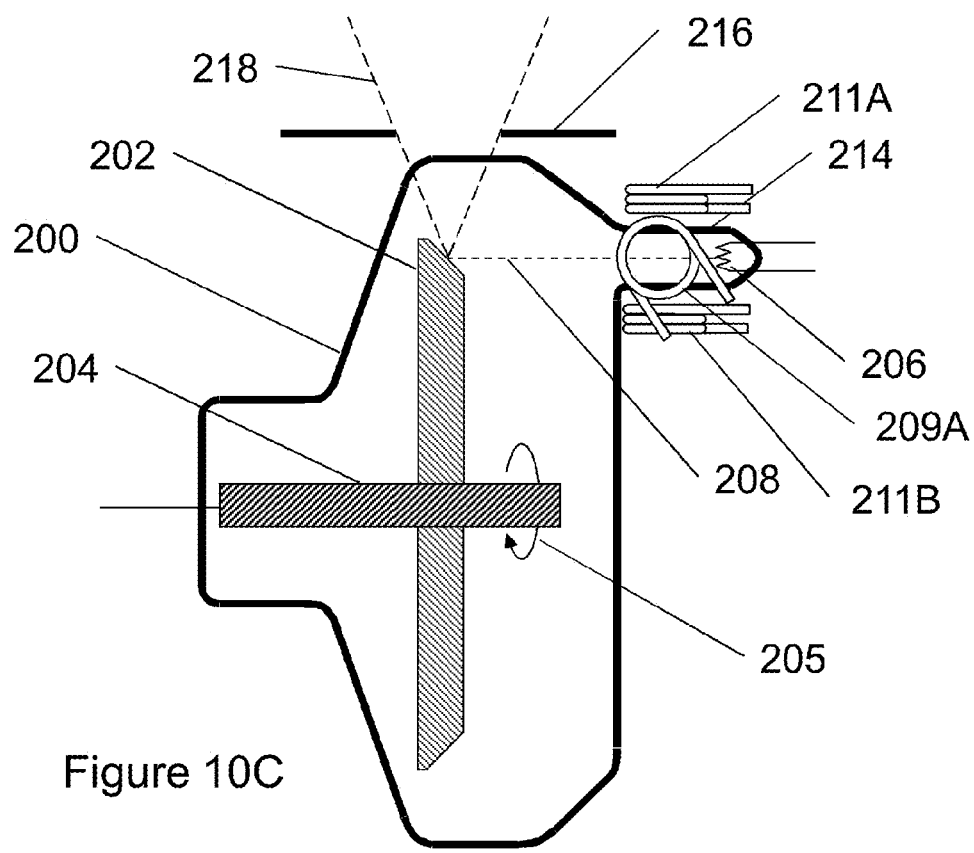
FIG. 10C illustrates a schematic x-ray tube with deflection coils only, without ferromagnetic cores.
Figure 10D:
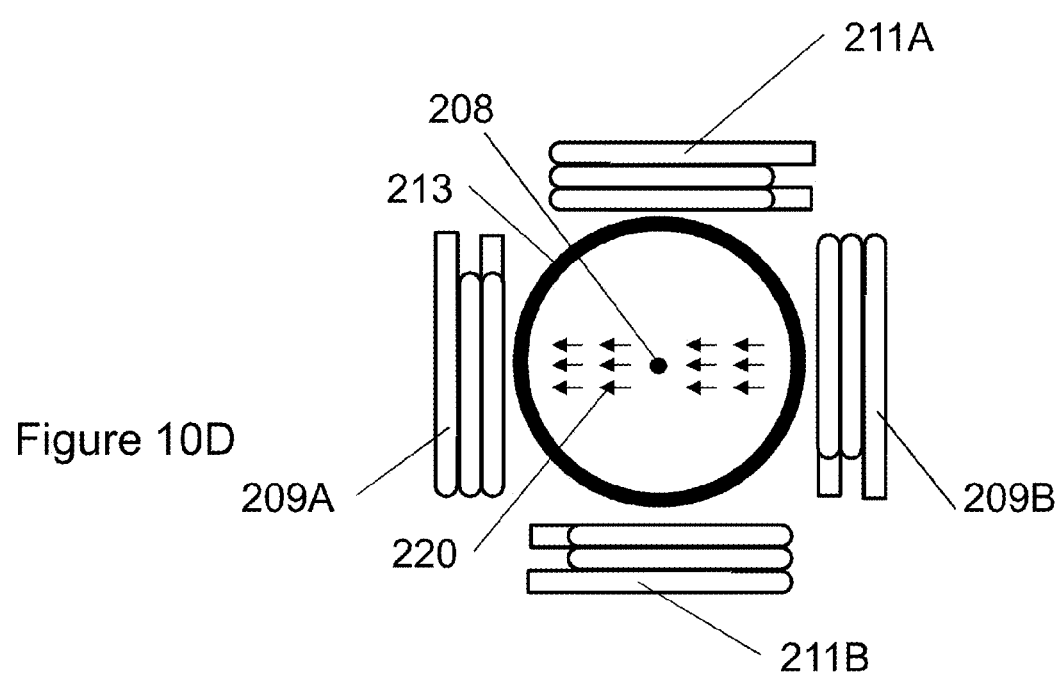
FIG. 10D illustrates a more detailed view of an arrangement of the deflection coils of FIG. 10C.

In FIGS. 10C and 10D the yokes are replaced with coils only (no ferromagnetic core is used). The coils are arranged so that electron beam 208 is parallel to the plane of the coils. In the example of FIG. 10D, when current is driven through coils 209A and 209B in one direction, a magnetic field 220 is created and thus, electron beam 208 passing perpendicular to this magnetic field id deflected vertically, as explained above in reference to FIG. 10B.

Figure 11:
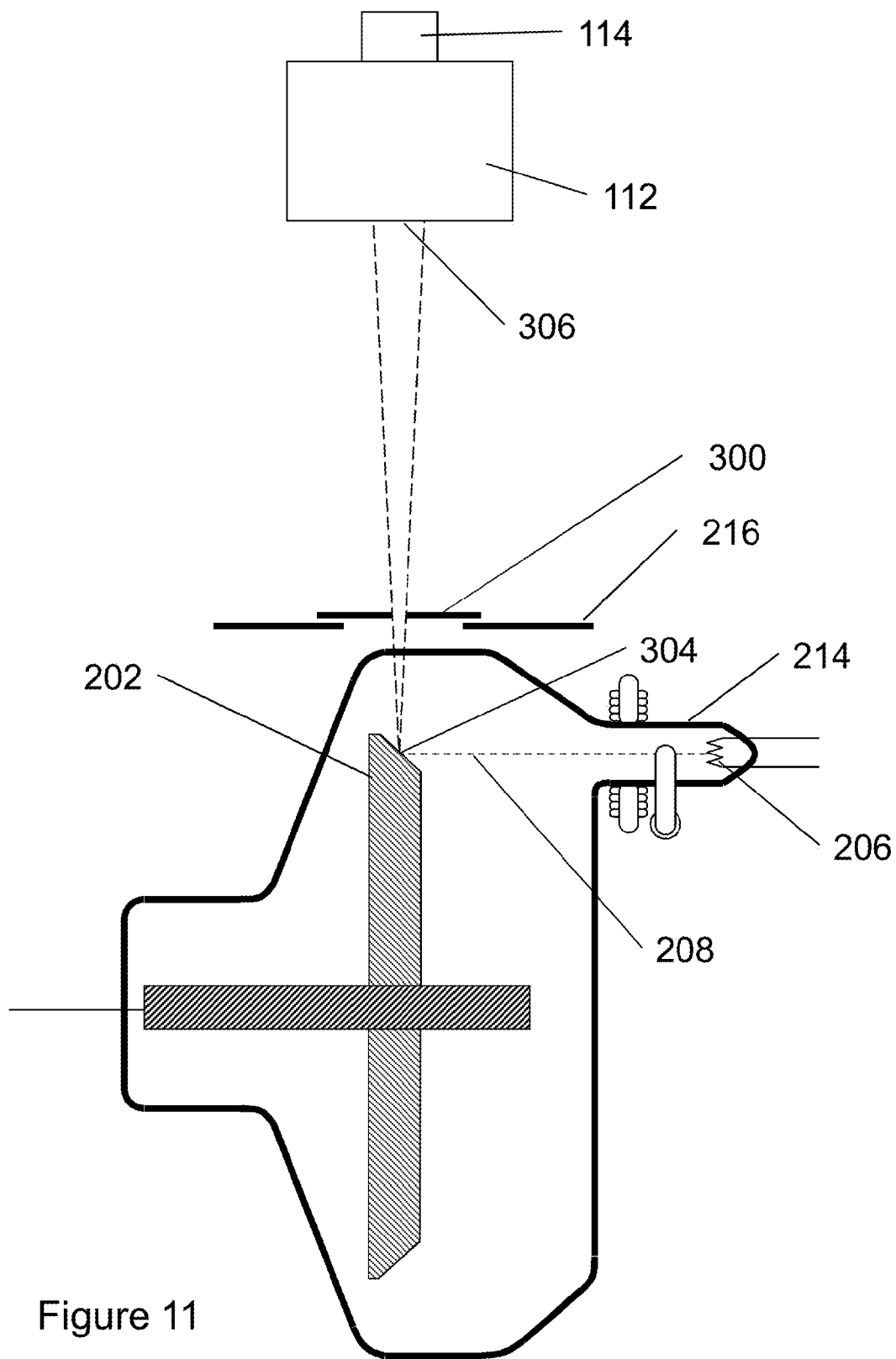
FIG. 11 illustrates an x-ray tube with a collimator configured to provide a relatively narrow cone of radiation at the center of the image intensifier input area.
Figure 12:
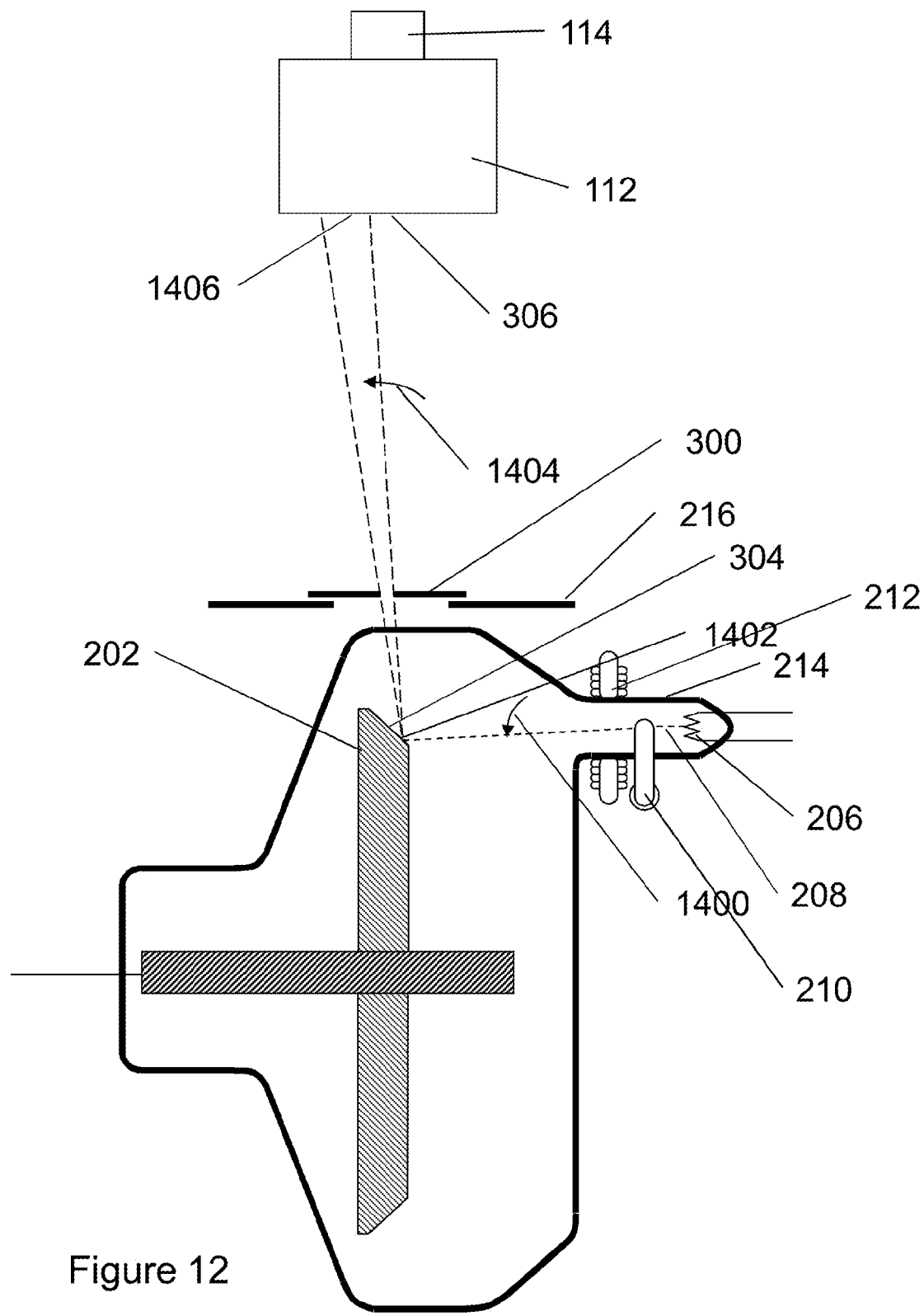
FIG. 12 illustrates the configuration of FIG. 11 with the electron beam deflected downwards and, as a result, the relatively narrow cone of radiation is deflected to the left side of the image intensifier input area.

FIG. 11 and FIG. 12 demonstrate how the x-ray tube of FIG. 10A and FIG. 10B is used to manipulate the direction of a relatively narrow x-ray beam. Reference is made now to FIG. 11. In the example of FIG. 11 no current is flowing through the coils of yokes 210 and 212 and therefore electron beam 208 is not exposed to a magnetic field and hits the anode at point 304. A small aperture collimator 300 is placed in the beam way to reduce the solid angle of the x-ray beam. For example, a collimator with a round aperture of 5 mm placed at a distance d=75 mm above point 304 produces an exposure of 50 mm in diameter on the input area of image intensifier 112 when the input area is at a distance D=750 mm above point 304. Distances d, D and diameter (or other dimension for other aperture geometry) can be manipulated to get the desired geometry.

In the arrangement of FIG. 11, where no magnetic field is applied, the x-ray beam originating from point 304 of the anode 202 expose an area 50 mm in diameter centered about point 306 on the input area of image intensifier 112. For D=1000 mm and d=10 mm, a horizontal deflection of electron beam 208 of 1.5 mm will displace the exposure area 150 mm on the input area of the image intensifier. In such a case, to generate 50 mm diameter exposure on the input area of the image intensifier, the aperture in the collimator should be 0.5 mm in diameter.

Reference is made now to FIG. 12.

In FIG. 12, electrical current is driven through coil 209 (see FIG. 10B) that deflects the electron beam downwards as shown by arrow 1400. As a result, the point where the electrons now hit the anode 202 has moved from position 304 of FIG. 11 to position 402. Due to the shift to the right in the point of origin of the x-ray beam, the whole beam direction rotates now anti-clock wise as shown by arrow 1404 and the center of the exposure area in the input area of image intensifier 112 shifts from point 306 of FIG. 11 to point 1406 of FIG. 12.

It would be appreciated by those skilled in the art that using this method, the narrow x-ray beam can by directed at any point on the input area of image intensifier 112. By controlling the currents in the coils of yokes 210 and 212 the 2-dimensional position of the exposure center (1406 of FIG. 12 and 306 of FIG. 11 can be set to any desired position on the input area of the image intensifier. By controlling the rate of change of the current in the coils, one can control the speed of motion of the exposure area though any desired path. The motion function (speed and location as a function of time) of the exposure area over the input area is fully controlled through the current in the coils of yokes 210 and 212. For example, driving yoke 210 and 212 using sine-wave function where yoke 212 sine-wave phase is delayed one π (180 degrees) relative to the sine-wave of yoke 210 will move the exposure area along an elliptic path on input area 112. The motion pattern can be designed to slow the x-ray beam in the specified ROI on input area 112 and move it faster over the rest of the input area thus getting a better exposure and a better image thereby in the ROI while reducing exposure and image quality elsewhere.

Figure 13A:
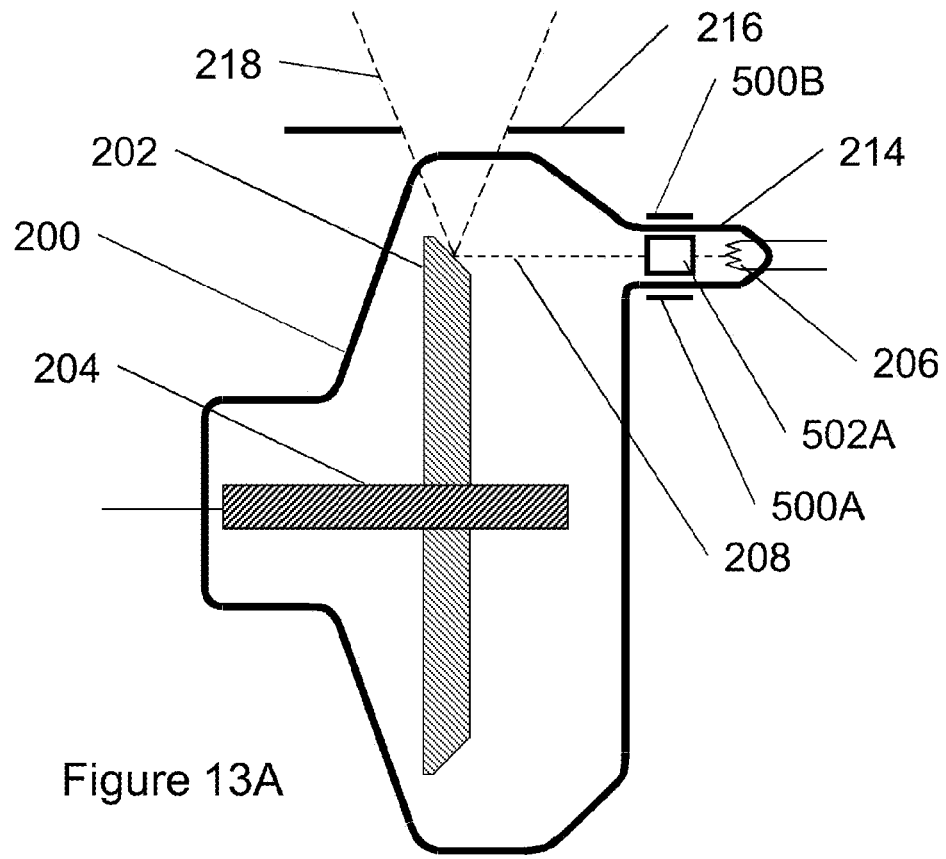
FIG. 13A illustrates a schematic x-ray tube with deflection plates.

Reference is made now to FIG. 13A.

FIG. 13A illustrates construction of conductive plates instead of yokes for the deflection of electron beam 208. Plates 500A and 500B operate to deflect electron beam 208 in the vertical direction and plates 502A and 502B (only plate 502A is visible in FIG. 13A) operate to deflect electronic beam 208 in the horizontal direction. The deflection is better understood in reference to FIG. 13B.

Figure 13B:
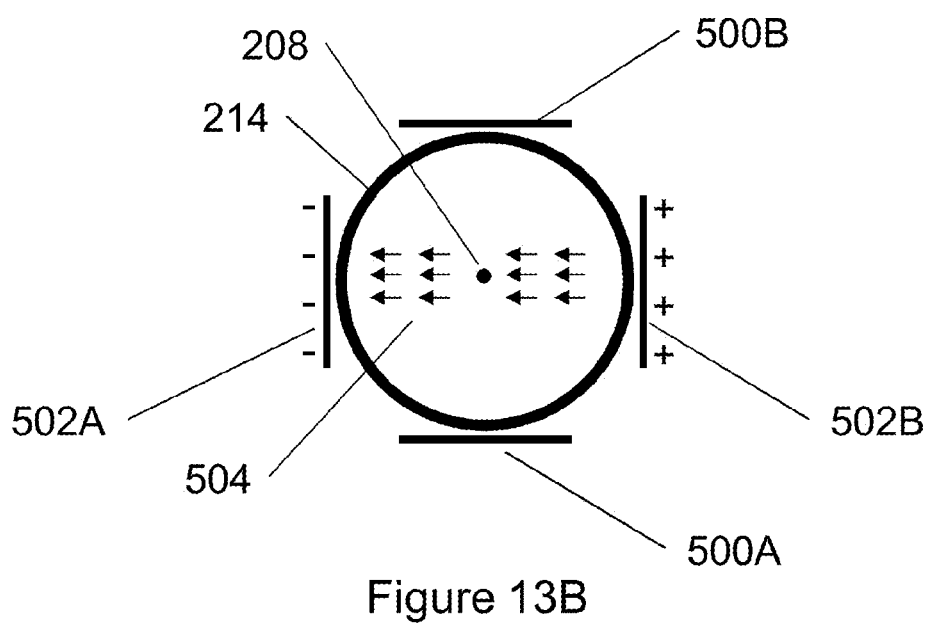
FIG. 13B illustrates a more detailed view of an arrangement of the deflection plates of FIG. 13A.

In the example of FIG. 13B, Left plate 502A is charged with a negative charge and right plate 502B is charged with a positive charge, inducing electrical field illustrated by arrows 504. As a result of this electrical field the electrons of electron beam 208 are deflected to the right. By using an opposite polarity on plates 502A and 502B electron beam 208 will be deflected to the left. Using plates 500A and 500B in the same way provides deflection of electron beam 208 in the vertical direction.

It would be appreciated that the magnitude of deflection of electron beam 208 is dependent on the potential difference between plates 500A and 500B and plates 502A and 502B.

It would also be appreciated that using only one plate for the horizontal deflection, such as plate 502A and charging it with positive or negative charge can also provide for the horizontal deflection of electron beam 208 and the x-ray tube can be constructed accordingly. The same holds for the vertical direction where only one of plates 500A or 500B can be used to vertically deflect electron beam 208.

Figure 14:
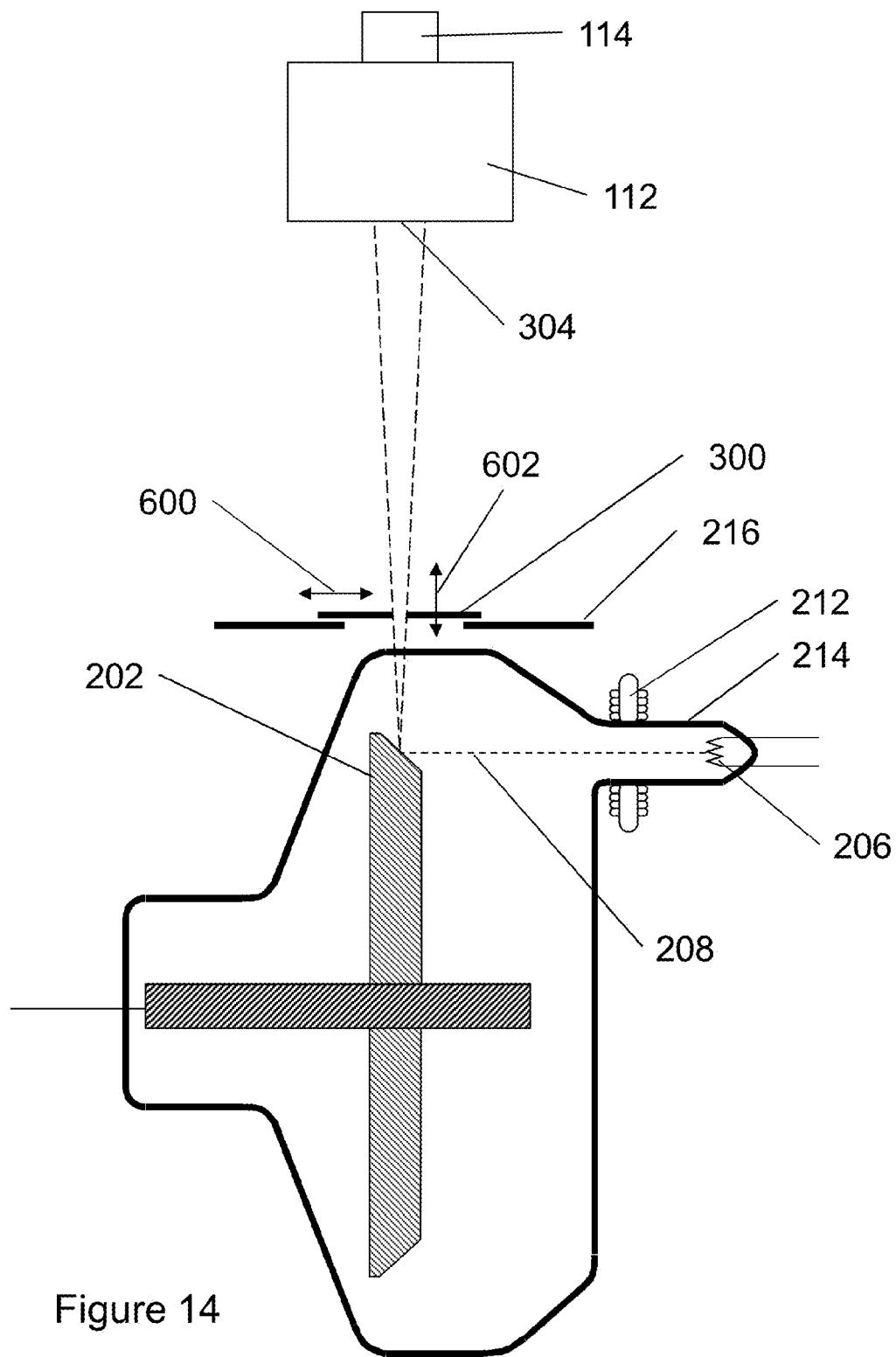
FIG. 14 illustrates an x-ray tube where the electron beam can be deflected in one direction and the collimator in another direction.

Reference is made now to FIG. 14.

In this example yoke 210 is removed and only yoke 212 is incorporated in the x-ray tube. With this assembly electron beam 208 can be deflected only horizontally, providing motion of the x-ray beam in direction perpendicular to the page. The other component of motion of the x-ray beam is provided here by the mechanical motion, preferably motorized, of collimator 300 in direction left/right as illustrated by arrow 600. By the combination of movements enabled by the yoke and in perpendicular direction by the movement of the collimator, the motion function of the exposed area can be fully controlled and support differential exposure in the ROI and outside the ROI.

By additionally enabling vertically controlled motion of collimator 300 as shown by arrow 602, the size of the exposed area, the radiation distribution over the exposure area and sensitivity of motion Vs control parameters can be modified. By moving collimator 300 upward the exposed area is reduced (the x-ray beam assumes smaller solid angle), the exposure area becomes more uniform and the sensitivity of position of the exposure area Vs electron beam deflection is reduced. These characteristics change in the opposite direction when collimator 300 is moved downwards.

A variable aperture collimator can be used to change the exposure area and it can also be used in combination with the above described vertical positioning of the collimator. This can enable, for example, moving the collimator upwards while increasing the aperture size to maintain the exposure area while changing the other parameters.

Figure 15:
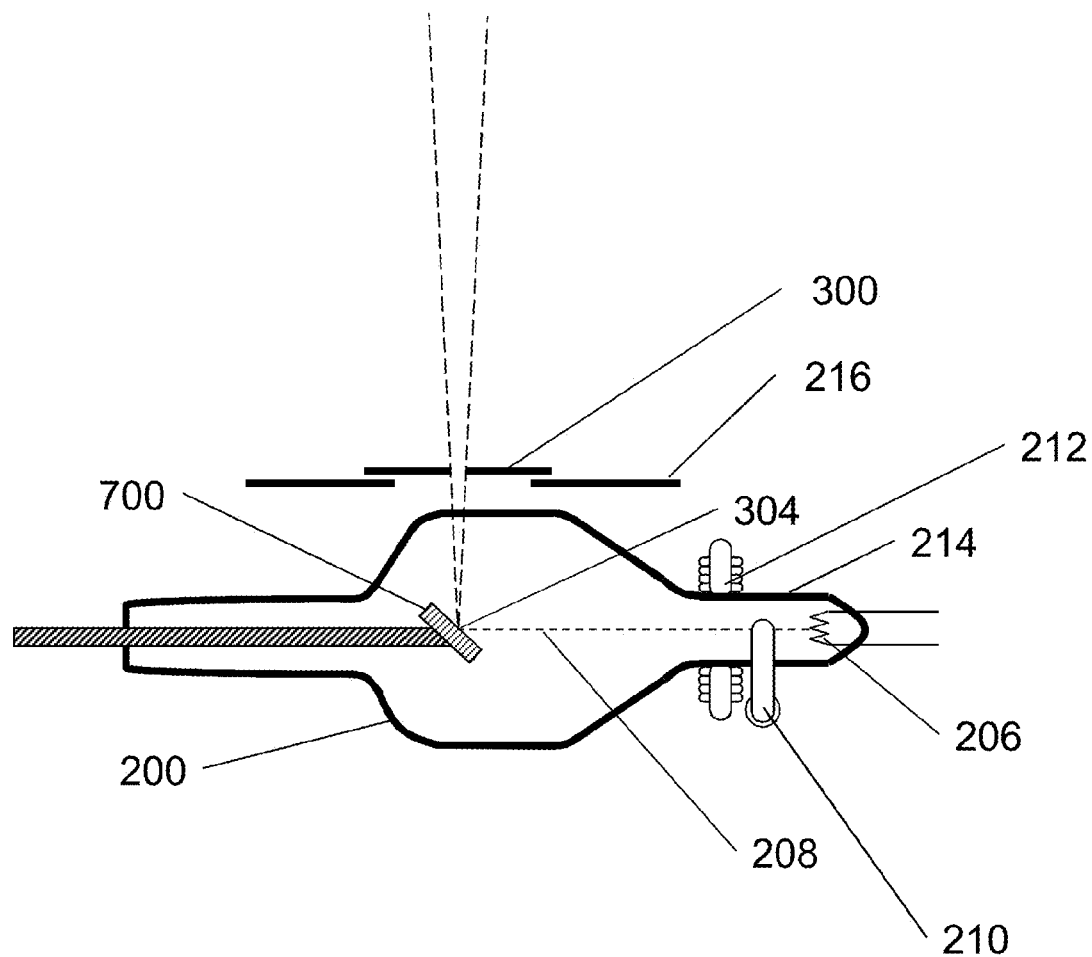
FIG. 15 illustrates an embodiment of the invention using a static-anode x-ray tube.

It would be appreciated that all the embodiments described above are not limited to rotating anode x-ray tubes and they can be implemented with static anode x-ray tubes without any difficulty. This option is illustrated in FIG. 15 where the static anode 700 is shown with the example of yokes 210 and 212.

To control the current of the yokes of the current invention, any controllable current source can be used. It is particularly convenient to use a digitally controlled current source to simplify the current manipulation using a computer or any other programmable device. An example for such a current source is MCP1631HV Digitally Controlled Programmable Current Source Reference Design by Microchip Technology Inc. Chandler, Ariz., USA.

According to embodiments of the present invention, the x-ray tube assembly may comprise a plurality of cathode assemblies capable of generating a plurality of electron streams towards one or more anodes (as described in U.S. Pat. No. 6,125,167, incorporated herein by reference). The multiple electron streams may be controlled electronically, as described above, to create multiple focal points for respective multiple ROIs, e.g. of more than one physician.

Figure 16A:
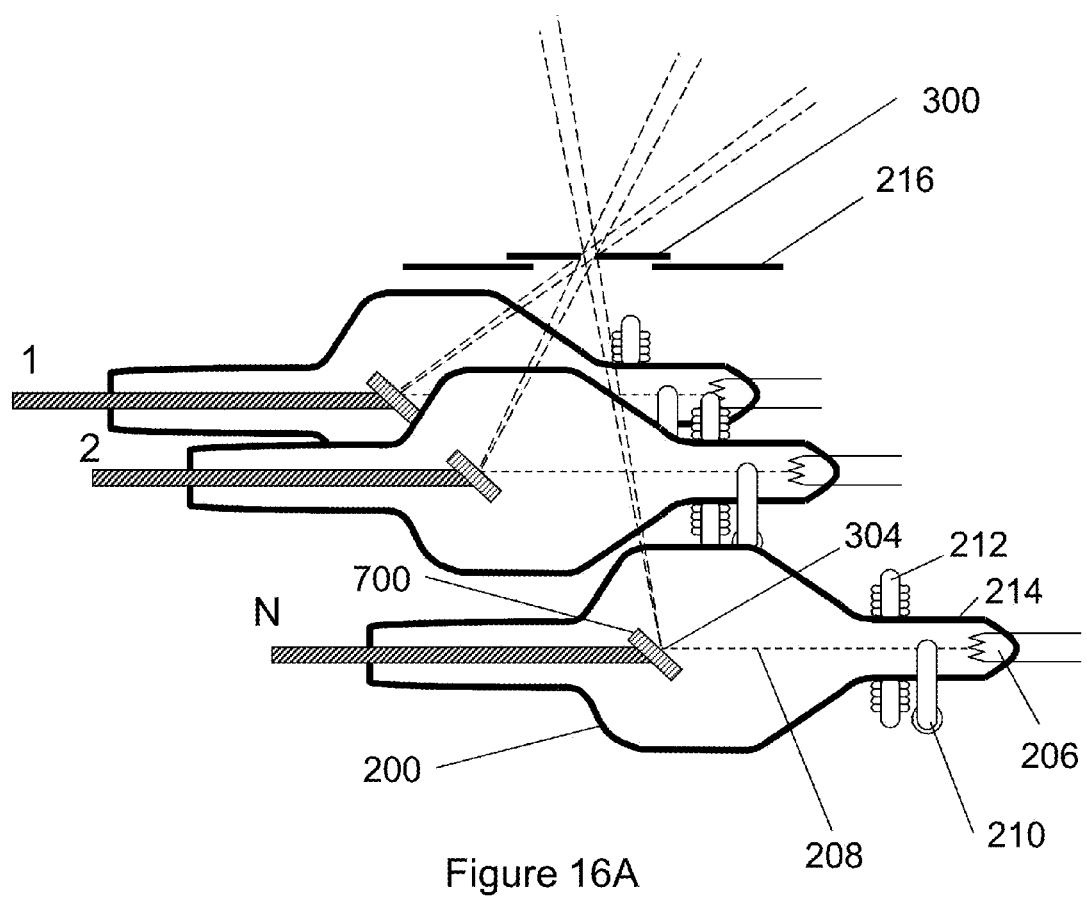
FIGS. 16A and 16B are exemplary embodiments of a plurality of cathode assemblies capable of generating a plurality of electron beams towards one or more anodes.
Figure 16B:
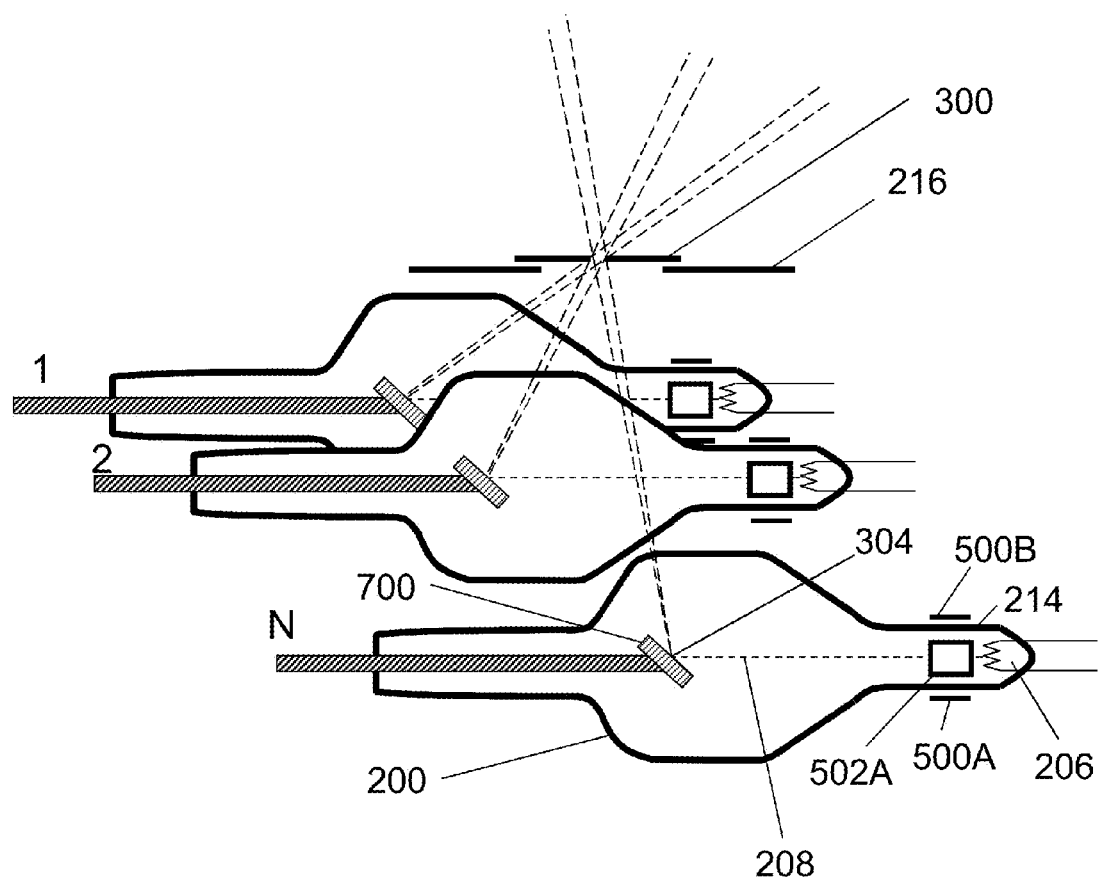

FIGS. 16A and 16B are exemplary embodiments of a plurality of cathode assemblies 206 capable of generating a plurality of electron beams 208 towards one or more anodes 700. The electron beams 1208 may be controlled in any one of the methods described above in conjunction with FIGS. 10A through 13B.

Figure 16C:
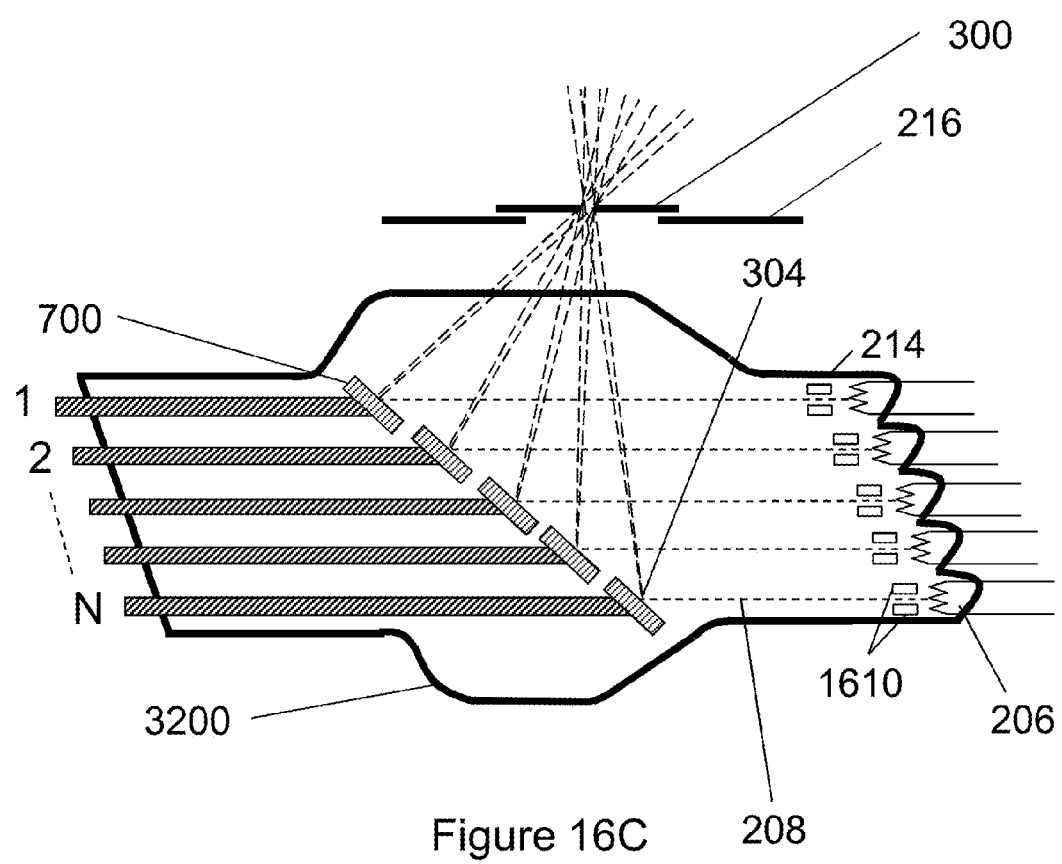
FIG. 16C is another exemplary embodiment of a plurality of cathode assemblies capable of generating a plurality of electron beams towards one or more anodes.

FIG. 16C is another exemplary embodiment of a plurality of cathode assemblies 206 capable of generating a plurality of electron beams 208 towards one or more anodes 700, wherein the cathodes and the anodes are encapsulated in a single X-ray tube assembly 3200. The electron beams 208 may be controlled (1610) in any one of the methods described above in conjunction with FIGS. 10A through 13B.

According to embodiments of the present invention, one or more anodes and one or more cathodes, may each be mechanically actuated in several degrees of freedom with translational and rotational axes of motion. Such actuation may be done remotely (outside the housing frames) or built-in within the X Ray tube containing frame. Such actuators may be electric motors or other types of actuators such as pneumatic, piezoelectric, etc. Such actuators may also be direct drive or geared as required to match torques/forces and velocities. The orientation/direction in space of each electron beam generated by each cathode (filament) is also being controlled (actuated) electronically by electromagnetic field generated by coils or other electromagnetic field sources, as described above in conjunction with FIGS. 10A through 13B. Such direction is controlled in multiple axes so as to electronically determine the landing point of the electron beam on the corresponding anode.

A controller 130 is used to coordinate the mechanical and/or the electronic actuation as described above. The controller 130 receives the defined required ROIs (which include: number, location, size and needed power—for each of the defined ROIs) and via software or firmware determines which subset of cathodes/anodes are to be energized as well as provide to each actuator the needed: timing, duration, range, velocities and all other parameters needed for the resulting electron beam array to produce the photon beam array as per the user specifications.

According to embodiments of the invention, controller 130 may select between the electronic beam deflection mode as described in conjunction with FIGS. 10A through 13B and the mechanical movement. The determination may depend, for example, on the required movement angle of the electron beam, where small movements may be implemented by electronic deflection while larger movements may be implemented mechanically.

It is also contemplated that the electron beam movement may be implemented by both methods, where a larger movement is implemented mechanically and electronic deflection is used for achieving accurate deflection resolution.

Figure 17A:
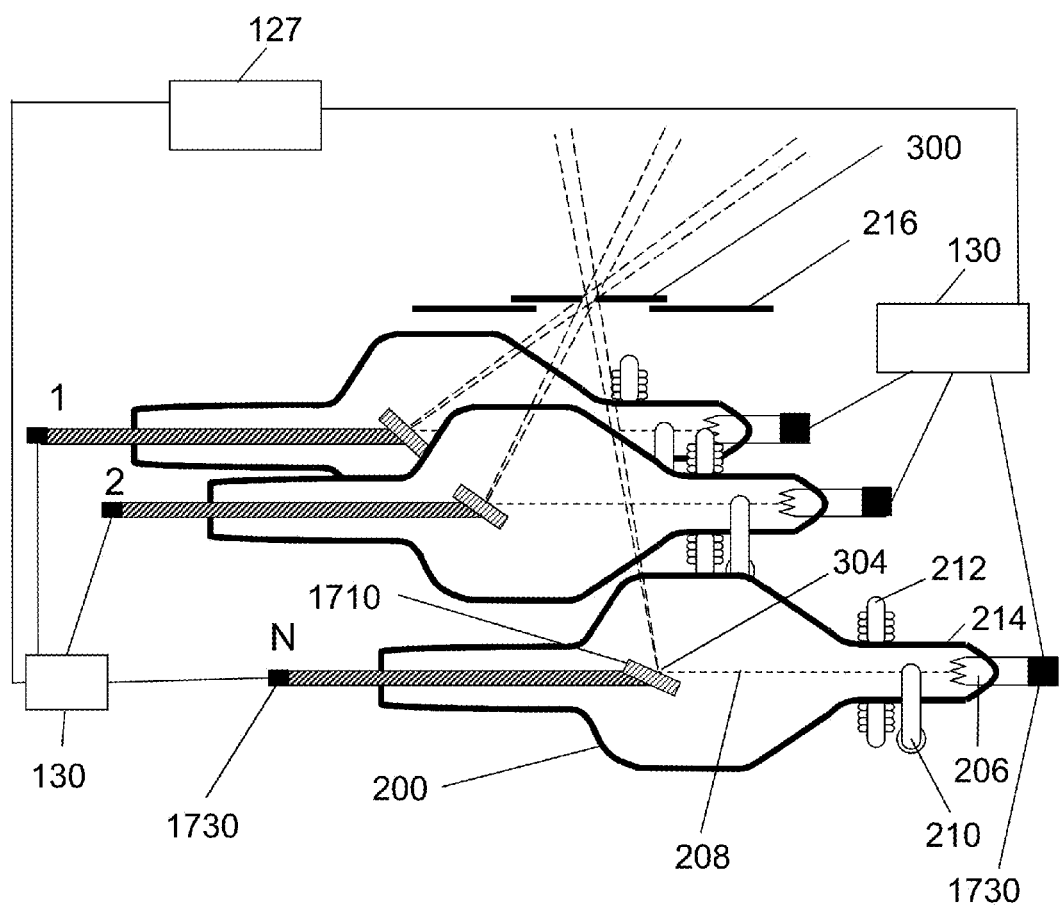
FIGS. 17A and 17B are exemplary embodiments of mechanically controlled anodes and cathodes each showing a different method of controlling the electron beam.
Figure 17B:
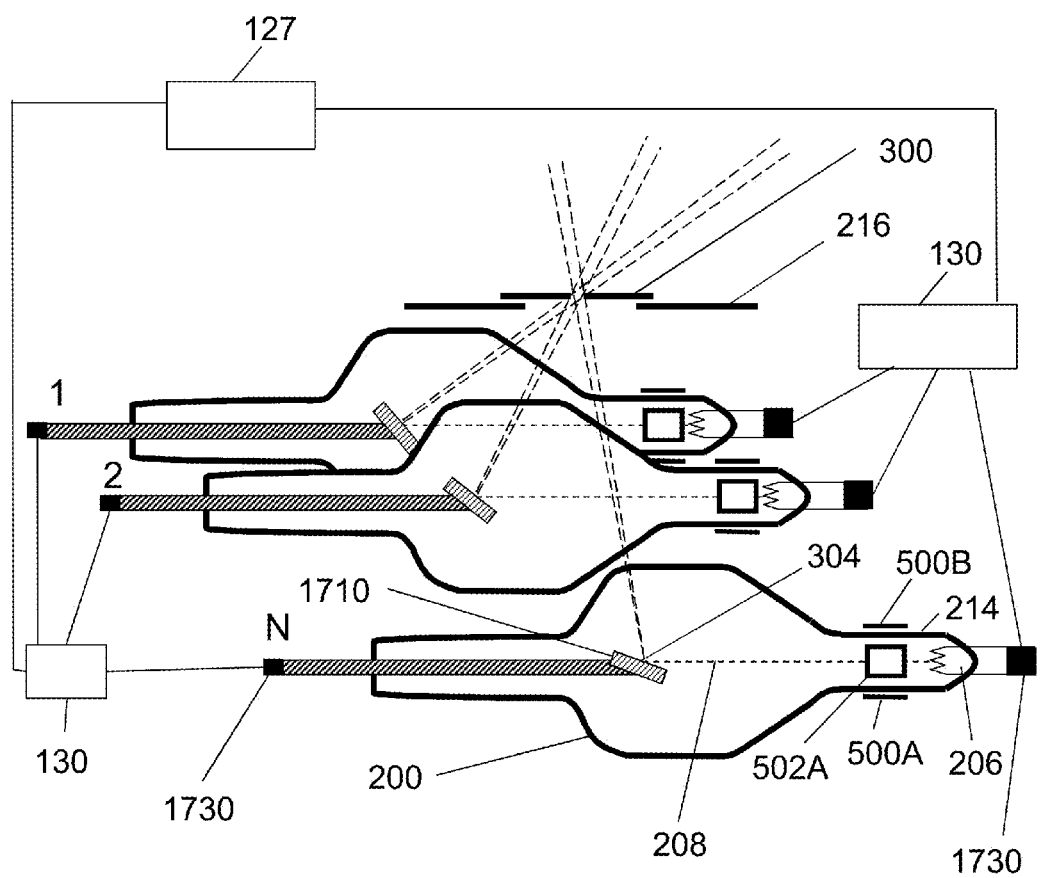

FIGS. 17A and 17B are exemplary embodiments of mechanically controlled anodes 1710 and cathodes 206. The anode(s) and\or the cathode(s) are mechanically controlled by actuators 1730 that are being controlled by controller 130. In addition, the electron beams may be controlled in any one of the methods that were described above in conjunction with FIGS. 10A through 13B.

Figure 17C:
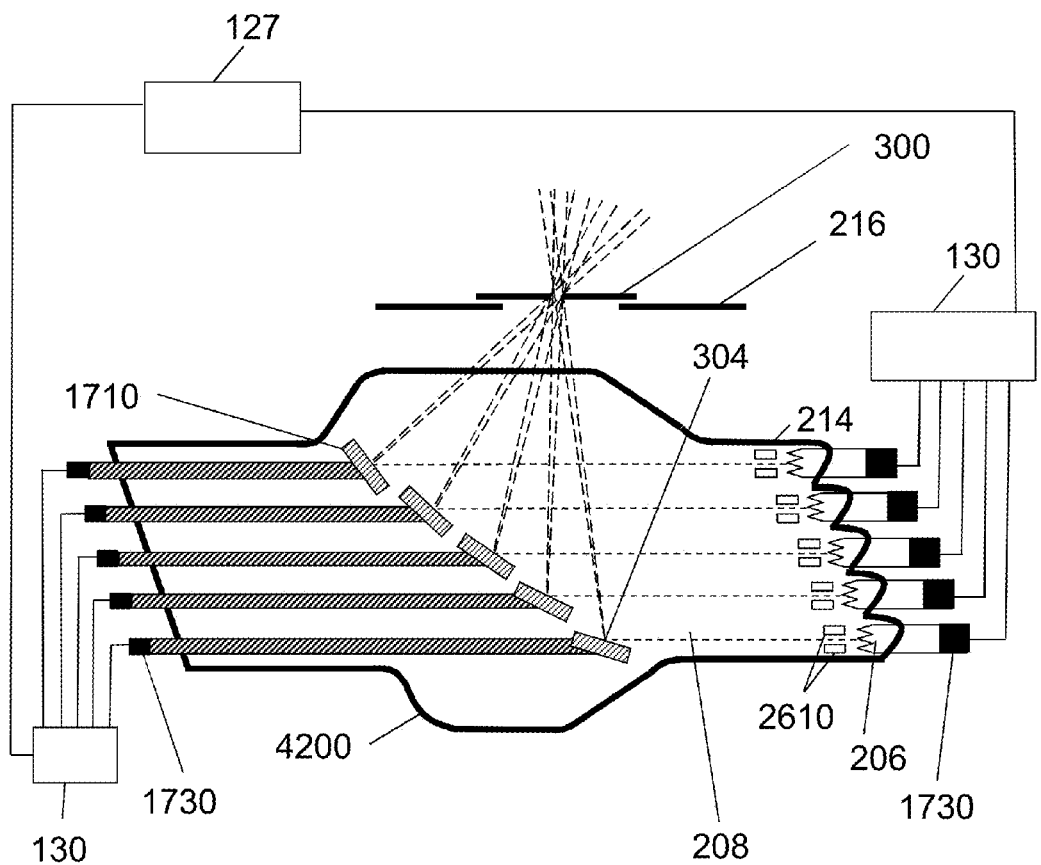
FIG. 17C is another exemplary embodiment of mechanically controlled anodes and cathodes, wherein the cathodes and the anodes are encapsulated in a single X-ray tube.

FIG. 17C is an exemplary embodiment of mechanically controlled anodes 1710 and cathodes 206, wherein the cathodes and the anodes are encapsulated in a single X-ray tube assembly 4200. In this embodiment, the electron beams 208 may be controlled (2610) in any one of the methods that were described above in conjunction with FIGS. 10A through 13B.

According to embodiments of the present invention, the current supplied to the cathode may be controlled.

Figure 18:
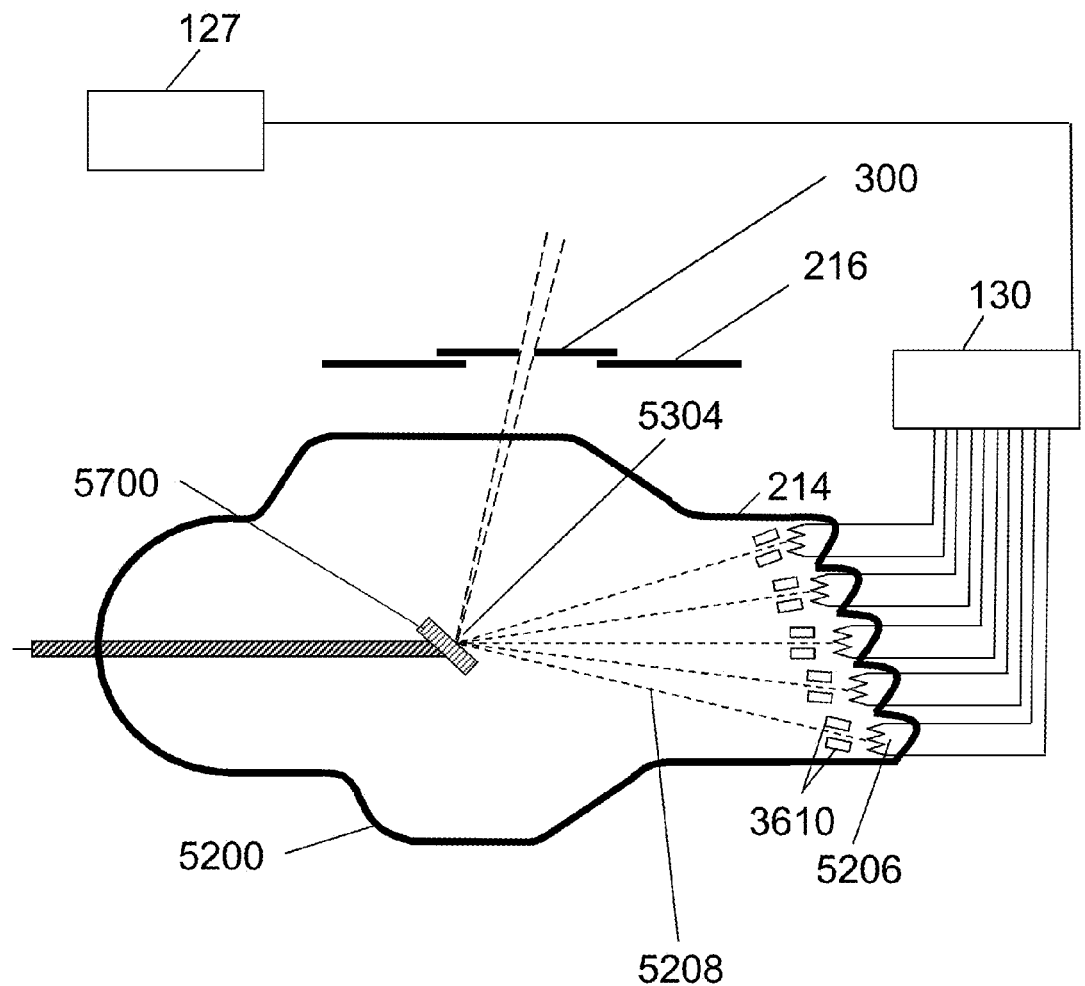
FIG. 18 is an exemplary embodiment of a plurality of cathodes and an anode encapsulated in a single X-ray tube.

FIG. 18 is an exemplary embodiment of a plurality (N) of cathodes 5206 (e.g. 5) and an anode 5700 encapsulated in a single X-ray tube assembly 5200. In this embodiment, each cathode receives a partial heating current that causes it to generate an electron beam 5208, from this cathode to the anode, that equals 1/N (e.g. ⅕) of the total electron beam current required at point 5304. The N electron beams 5208 are aimed to the same focal point 5304, thus providing together the same intensity as one electron beam generated by one cathode receiving the a full heating current level to enable generating the full electron beam current. As a result, the power dissipation and the heating of each of the cathodes are reduced, thus extending the "life" of the cathode. It would be appreciated that the electron beam currents of the plurality of the cathodes do not have to be equal to each other and at least one electron beam current from at least one cathode may be different from at least one electron beam current from at least one other cathode. Each cathode may be operated to provide any electron beam current from zero to the full required current at point 5304. Typically, the operation of the system will be conducted such that the sum of the electron beam currents from the individual cathodes will be equal to the total desired electron beam current at the anode with typical deviation as best suits the application. In most applications such a deviation will be up to +/−50%.

The heating current is controlled by controller 130. In this embodiment, the electron beams may also be controlled (3610) in any one of the methods that were described in conjunction with FIGS. 10A through 13B. The anode and the cathode(s) may also be mechanically controlled as described above in conjunction with FIG. 17A through 17C (not shown).

According to embodiments of the present invention, the system may provide a stereoscopic ROI image of an object. In order to provide such image, the system may capture two images of the same object, from two different perspectives in two different points in time (t1 and t2). Assuming that the time lapse between t1 and t2 is small enough such that no significant object motion occurs within it, standard stereoscopic processing of the two 2D images is used to create the stereoscopic ROI image. The image may then be viewed via lenticular lens, by designated glasses or by any other method known in the art.

Figure 19A:
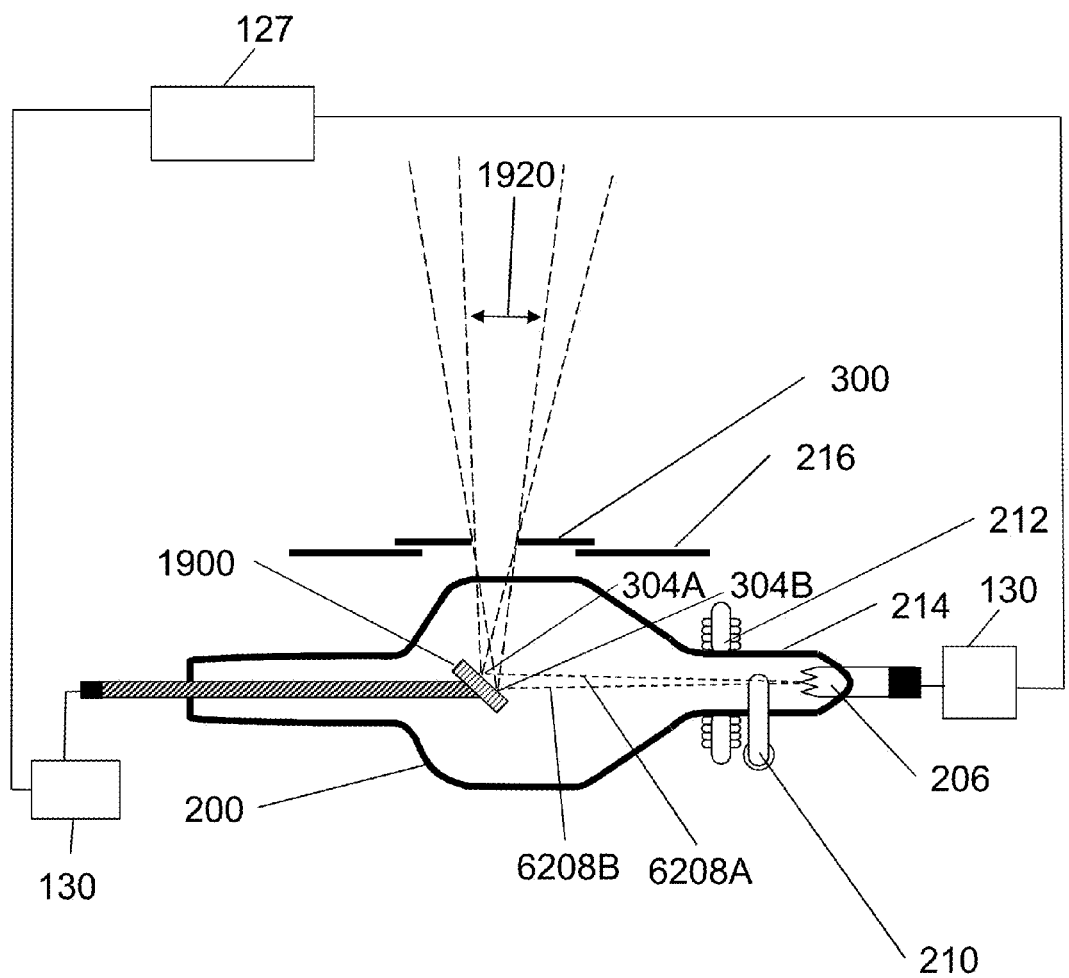
FIGS. 19A and 19B are exemplary embodiments of a system for providing a stereoscopic ROI image.
Figure 19B:
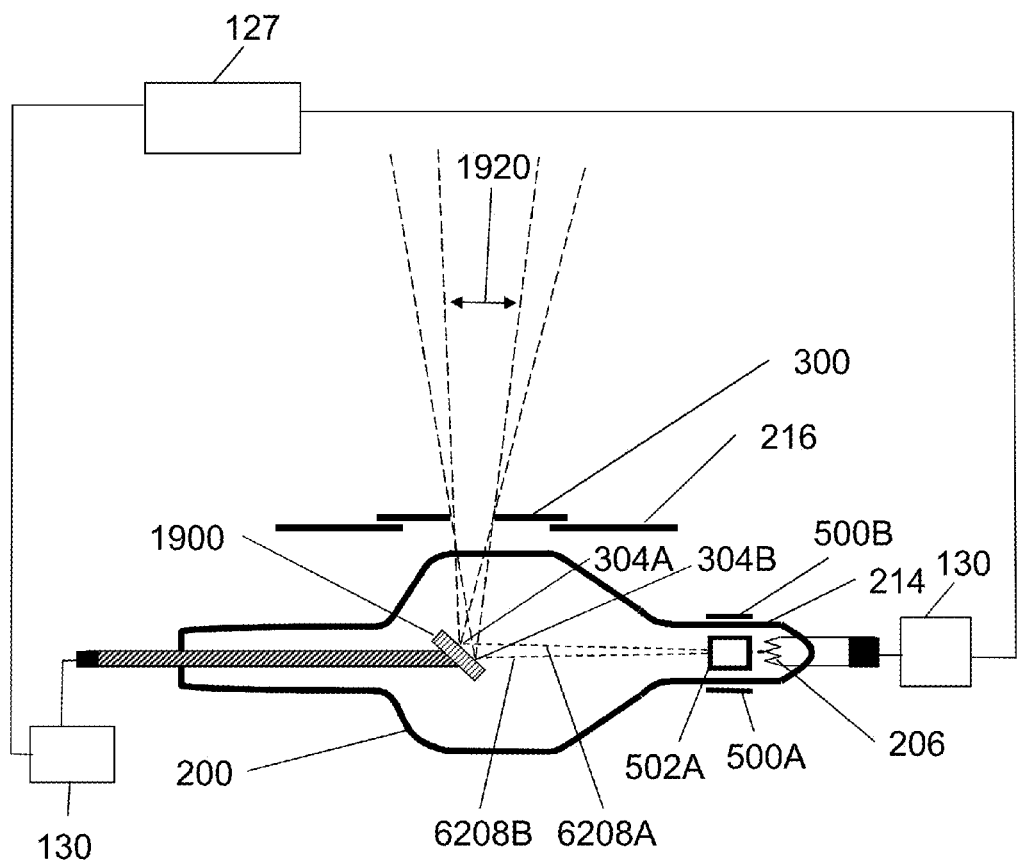

FIGS. 19A and 19B are exemplary embodiments of the system for providing a stereoscopic ROI image. In these embodiments, the cathode 206 generates an electron beam 6208A towards focal point 304A at t1 and an electron beam 6208B towards focal point 304B at t2. While the object to be scanned is mounted within the overlapping area 1920, two images from two different perspectives are obtained.

The electron beams 6208A and 6208B may be controlled in any one of the methods described above in conjunction with FIGS. 10A through 13B. The beams may also be controlled by mechanically controlled anode and\or cathode as described above in conjunction with FIGS. 17A and 17B.

Figure 19C:
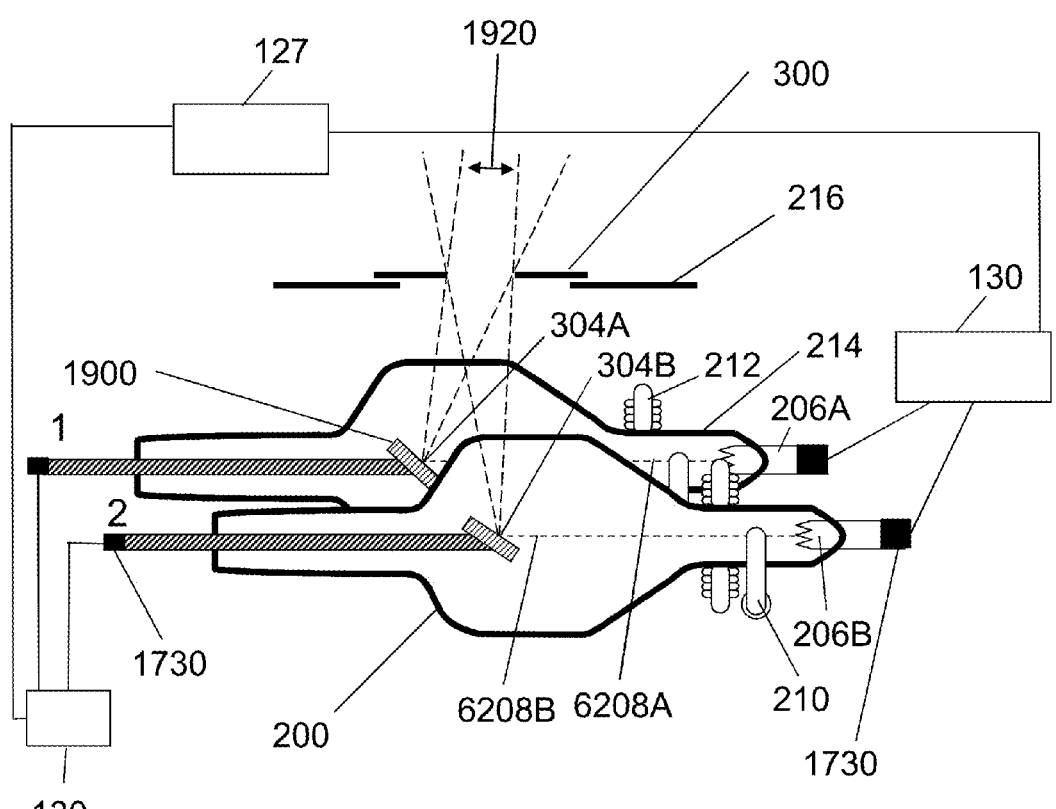
FIGS. 19C and 19D are exemplary embodiments of the process of FIGS. 19A and 19B, with two different X-ray tubes.
Figure 19D:
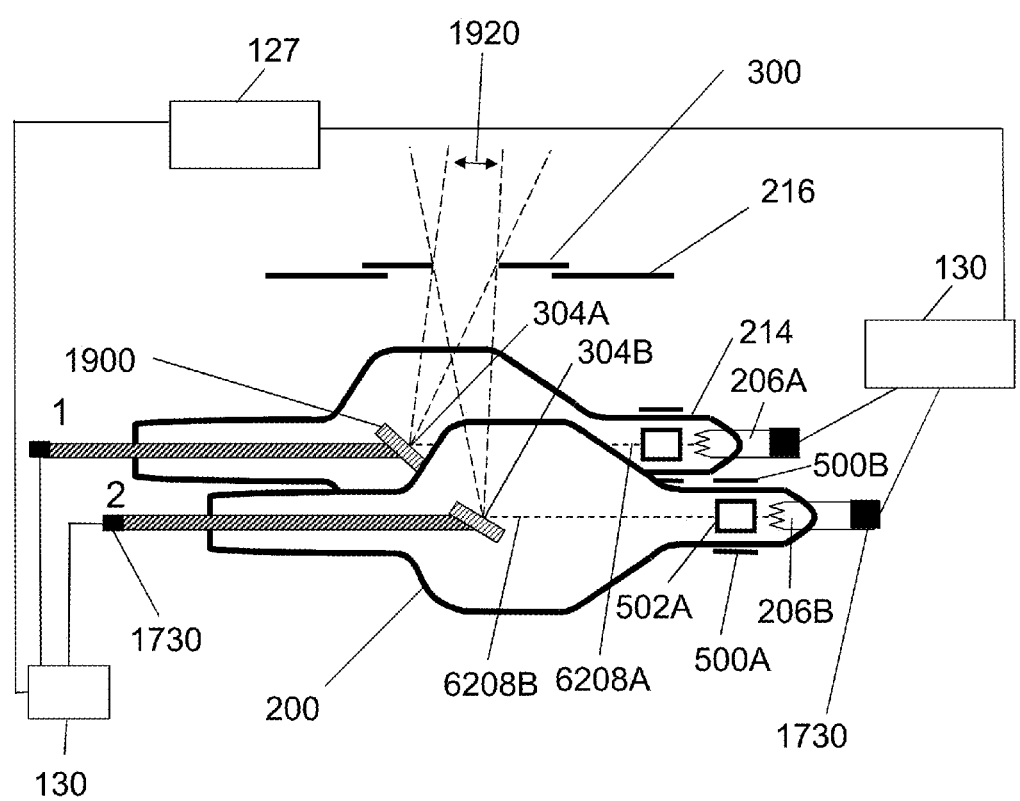

FIGS. 19C and 19D are exemplary embodiments of the same process that was explained in conjunction with FIGS. 19A and 19B, but with two different X-ray tube assemblies. In these embodiments, the cathode 206A generates an electron beam 6208A towards focal point 304A at t1 and the cathode 206B generates an electron beam 6208B towards focal point 304B at t2. While the object to be scanned is mounted within the overlapping area 1920, two images from two different perspectives are obtained.

The electron beams 6208A and 6208B may be controlled in any one of the methods described above in conjunction with FIGS. 10A through 13B. The beams may also be controlled by mechanically controlled anodes and\or cathodes as described above in conjunction with FIGS. 19A and 19B.

Figure 19E:
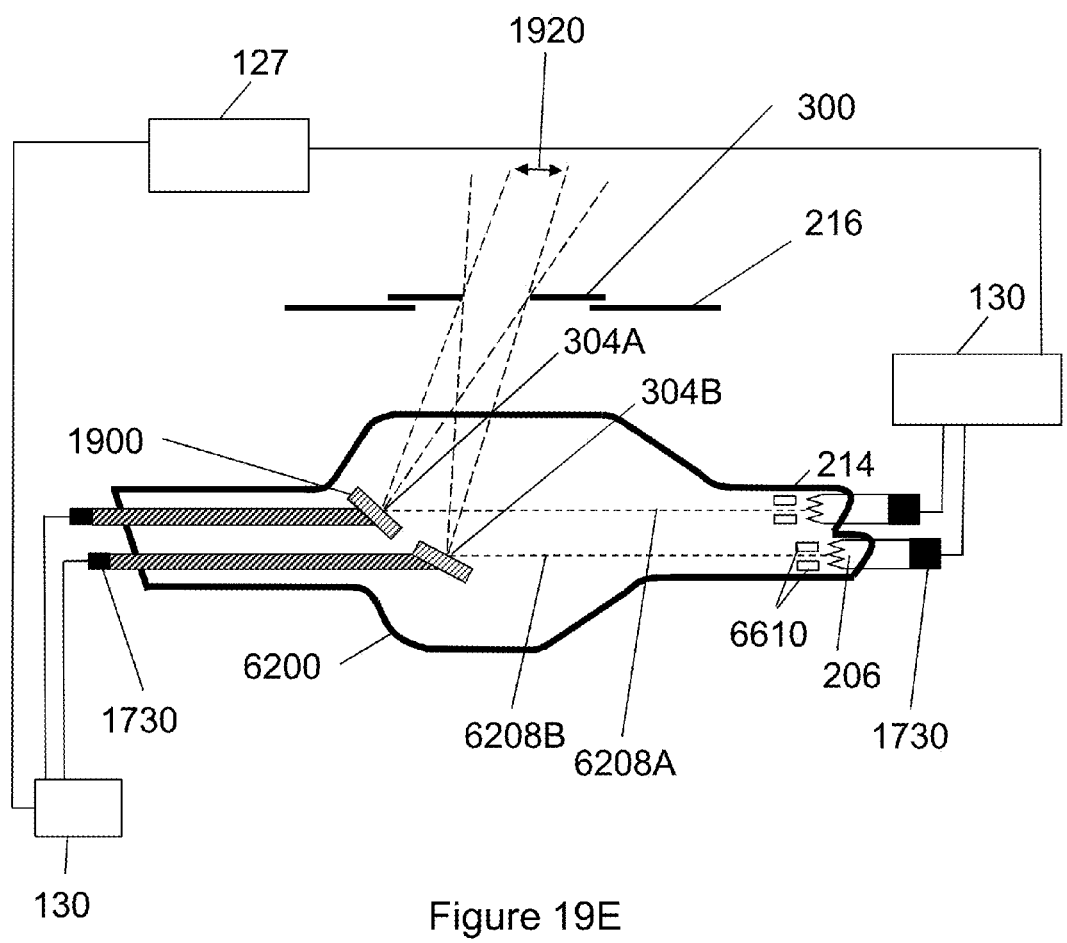
FIG. 19E is an exemplary embodiment of the process of FIGS. 19C and 19D, with two sets of anodes and cathodes encapsulated in a single X-ray tube.

FIG. 19E is an exemplary embodiment of the same process that was explained in conjunction with FIGS. 19C and 19D, but with two sets of anodes and cathodes encapsulated in a single X-ray tube assembly 6200.

According to embodiments of the present invention, the two different perspectives may be achieved by capturing the first image, moving the C arm to a different position and capturing the second image.

It will be appreciated that the embodiments of FIGS. 19A-19E are not limited to capturing two images, from two different perspectives, at two different times via two cathodes, generating two electron beams, aimed to two collision locations. The system and method may support capturing a plurality of images, from a plurality of different perspectives, at a plurality of different times via a plurality of cathodes, generating a plurality of electron beams, aimed to a plurality of collision locations.

While the foregoing has been with reference to a particular embodiment of the invention, it will be appreciated by those skilled in the art that changes in this embodiment may be made without departing from the principles and spirit of the disclosure, the scope of which is defined by the appended claims.

The invention claimed is:

1. An x-ray system comprising:
   at least one x-ray tube assembly;
   a collimator forming an aperture;
   an image detector;
   a monitor configured to display detected images;
   means for determining the location of at least one Region of Interest (ROI) comprising image parts of a patient on said displayed image;
   a first controller connected with said means for determining the location of said at least one ROI;
   an image processing unit connected with said image detector, said monitor and said first controller, said image processing unit configured to modify the detected image for display on said monitor according to the image parts in said at least one ROI;
   each x-ray tube assembly comprising a plurality of cathodes; and
   at least one anode;
   a second controller connected with said first controller and with said at least one x-ray tube assembly, said second controller configured to control operating parameters of each one of said at least one x-ray tube assembly, said parameters comprising at least one collision location of electrons emitted from said plurality of cathodes on said at least one anode in reference to said collimator aperture; and
   means for controlling the directions of emitted x-ray beams.

2. The x-ray system of claim 1, wherein said means for controlling the directions of emitted x-ray beams are selected from the group consisting of at least one electromagnetic device and at least one mechanical actuator.

3. The x-ray system of claim 2, wherein said at least one mechanical actuator is selected from the group consisting of: electric motors, pneumatic actuators and piezoelectric actuators.

4. The x-ray system of claim 2, wherein said second controller is configured to selectively deploy at least one of: said at least one electromagnetic device, said at least one mechanical actuator and each one of said plurality of cathodes' current for determining said at least one collision location.

5. The x-ray system of claim 4, wherein each one of said plurality of cathodes' current equals to a total current divided by the number of said plurality of cathodes and wherein said electron beams are directed to the same collision location.

6. The x-ray system of claim 4, wherein said selectively deploying comprises deploying at least one of said at least one electromagnetic device and said at least one mechanical actuator according to movement angles required by said at least one ROI.

7. The x-ray system of claim 2, wherein said collimator is configured to form an aperture limiting a solid angle of an x-ray beam emitted from each of said at least one anode.

8. The x-ray system of claim 7, wherein a current in each of the electromagnetic devices is set to control a direction of said solid angle of each of said x-ray beams.

9. The x-ray system of claim 7, wherein said aperture is movable in a plane generally parallel to a surface of the collimator.

10. The x-ray system of claim 9, wherein said first controller is further configured to calculate a location and size of said collimator aperture according to said determined locations of the at least one ROI.

11. The x-ray system of claim 7, wherein said collimator is movable in a plane generally perpendicular to a surface of the collimator.

12. The x-ray system of claim 1, wherein said means for determining the location of said at least one ROI comprise at least one eye tracker.

13. The x-ray system of claim 1, wherein said first controller is further configured to calculate collision locations of electrons emitted from the plurality of cathodes on the at least one anode according to said determined locations of said at least one ROI.

14. The x-ray system of claim 1, wherein said plurality of cathodes and at least one anode are encapsulated in a single x-ray tube assembly.

15. The x-ray system of claim 1, wherein said at least one anode comprises a plurality of anodes.

16. The x-ray system of claim 15, wherein said at least one x-ray tube assembly comprises a plurality of x-ray tube assemblies.

17. The x-ray system of claim 16, wherein said plurality of cathodes and said plurality of anodes are encapsulated in said plurality of x-ray tube assemblies wherein each x-ray tube assembly comprises at least one anode and at least one cathode.

* * * * *